US012777012B2

(12) United States Patent
Goel et al.

(10) Patent No.: US 12,777,012 B2
(45) Date of Patent: Oct. 27, 2026

(54) DATA STREAMING AND AGGREGATION WITH CLIENT-INITIATED RECOVERY

(71) Applicant: Oracle International Corporation, Redwood Shores, CA (US)

(72) Inventors: Sachin Goel, Bothell, WA (US); Eugene Florintsev, Austin, TX (US); Aman Kumar Sharma, Mathura (IN); Stuart John Edmondston, North Kellyville (AU)

(73) Assignee: ORACLE INTERNATIONAL CORPORATION, Redwood Shore, CA (US)

( * ) Notice: Subject to any disclaimer, the term of this patent is extended or adjusted under 35 U.S.C. 154(b) by 0 days.

(21) Appl. No.: 19/050,626

(22) Filed: Feb. 11, 2025

(65) Prior Publication Data

US 2026/0081889 A1 Mar. 19, 2026

(30) Foreign Application Priority Data

Sep. 13, 2024 (IN) ............................ 202441069381

(51) Int. Cl.

| | |
|---|---|
| ***H04L 12/26*** | (2006.01) |
| ***G10L 15/26*** | (2006.01) |
| ***G16H 15/00*** | (2018.01) |
| ***H04L 12/24*** | (2006.01) |
| ***H04L 51/23*** | (2022.01) |

(52) U.S. Cl.
CPC .............. *H04L 51/23* (2022.05); *G10L 15/26* (2013.01); *G16H 15/00* (2018.01)

(58) Field of Classification Search
CPC ......... H04L 51/23; H04L 12/26; H04L 12/24; G16H 15/00; G10L 15/26
(Continued)

(56) References Cited

U.S. PATENT DOCUMENTS 9,069,746 B2 6/2015 Ash et al.
9,432,251 B2 * 8/2016 Newman ............... H04L 1/1864
(Continued)

FOREIGN PATENT DOCUMENTS

CN 114448588 B 1/2024

OTHER PUBLICATIONS

"AI Soap Note Generator", Available online at: https://screenapp.io/features/ai-soap-note-generator, Accessed from internet on Sep. 24, 2024, pp. 1-10.
(Continued)

*Primary Examiner* — Jude Jean Gilles
(74) *Attorney, Agent, or Firm* — Kilpatrick Townsend & Stockton LLP

(57) ABSTRACT

Techniques are disclosed for data streaming and aggregation with client initiated recovery. In an example method, a client device provides, to a computing system, a first data message including a first sequence number, a first timestamp, and a first payload, the first sequence number indicating a first position within the audio data stream to which the first payload corresponds. The client device stores the first data message in a buffer of the client device, the buffer comprising one or more buffered data messages. The client device determines a first error condition for the first data message based on at least one of the one or more buffered data messages or a first acknowledgement status of the first data message. Responsive to determining the first error condition for the first data message, the client device re-provides, to the computing system, the first data message.

20 Claims, 13 Drawing Sheets

(58) Field of Classification Search
USPC .......................................................... 709/206
See application file for complete search history.

(56) References Cited

U.S. PATENT DOCUMENTS

| | | | |
|---|---|---|---|
| 11,158,411 B2 | 10/2021 | Koll et al. | |
| 11,670,408 B2 | 6/2023 | Pinto | |
| 11,894,140 B2 | 2/2024 | Strader et al. | |
| 2012/0030369 A1 | 2/2012 | Lamba et al. | |
| 2018/0150371 A1* | 5/2018 | Gintis | G06F 11/2733 |
| 2022/0091815 A1 | 3/2022 | Tumu et al. | |
| 2022/0254354 A1 | 8/2022 | Liang | |
| 2024/0069855 A1 | 2/2024 | Abhishek et al. | |

OTHER PUBLICATIONS

"AI-Powered Ambient Listening Technology That's Transforming Healthcare", Available online at: https://sunoh.ai/blog/ai-powered-ambient-listening-technology-thats-transforming-healthcare/, Jan. 18, 2024, pp. 1-4.

"AWS Kinesis Data Streams", Available online at: https://medium.com/@himanshu66/aws-kinesis-data-streams-cdec4adb9450, Jan. 28, 2024, pp. 1-21.

"How Sunoh AI Works", Available online at: https://sunoh.ai/how-sunoh-works/, Accessed from internet on Sep. 24, 2024, pp. 1-4.

"Medical Note-Taking AI Tool", Available online at: https://screenapp.io/use-cases/doctors-and-medical, Accessed from internet on Sep. 24, 2024, pp. 1-8.

"Unidirectional Streams", Available online at: https://datatracker.ietf.org/meeting/interim-2017-quic-02/materials/slides-interim-2017-quic-02-sessa-quic-unidirectional-00, Jun. 2017, pp. 1-16.

"Using Streams", Available online at: https://microsoft.github.io/msquic/msquicdocs/docs/Streams.html, Sep. 24, 2024, pp. 1-5.

Payne et al., "Using Voice to Create Hospital Progress Notes: Description of a Mobile Application and Supporting System Integrated With a Commercial Electronic Health Record", Journal of Biomedical Informatics, vol. 77, Available online at: https://www.sciencedirect.com/science/article/pii/S1532046417302745, Jan. 2018, pp. 91-96.

* cited by examiner

800

DATA STREAMING AND AGGREGATION WITH CLIENT-INITIATED RECOVERY

CROSS-REFERENCE TO RELATED APPLICATIONS

The present application claims the benefit of and priority to Indian Provisional Application No. 202441069381, filed Sep. 13, 2024, the entire contents of which are incorporated herein by reference for all purposes.

BACKGROUND

A client device can be used to collect audio data and relay the data to a remote server for processing. For example, a client device such as a smartphone can be used to stream an in-progress audio recording or a completed audio recording to a remote server over a network for transcription, conversion into other formats, summarization, and so on. Such applications may be found in, for example, the healthcare context, in which a healthcare provider verbally interacts with a patient and a client device records the interaction. The sequence of verbal interactions between provider and patient can include a variety of useful information that can be extracted from the recording.

The in-progress audio recording or completed audio recording can be sent over a network using certain network protocols. For example, the audio recording can be segmented and then sent over a network, one segment at a time, as a data stream. However, if the remote server or the network becomes unavailable during the segmented sending, this approach can result in an incomplete or corrupted transmission. In some cases, where the remote server detects an incomplete or corrupted transmission, the server can request that the client device re-send the audio recording.

BRIEF SUMMARY

Techniques are disclosed herein for data streaming and aggregation with client-initiated recovery. In some examples, a client device can stream audio data that includes multiple data messages to a remote server while audio is being recorded and/or after the recording of the audio is completed. The data messages can include a sequence number, a timestamp, and a payload, where the sequence number indicates the position of the payload within the audio data stream. The client device can then provide the data messages to the remote server. The client device can also store a copy of the data messages in a local buffer. The data messages may be acknowledged by the remote server and accordingly removed from the buffer. However, in some cases, certain kinds of network or system errors may occur that prevent an acknowledgement from being sent by the remote server or from being received by the client device. In that case, an error condition can be identified, by the client device, for certain data messages based on a lack of acknowledgement, a passage of a predetermined time, and/or other criteria. Identified messages associated with the error condition can be re-provided to the remote server using the retained copy in the buffer. The remote server may include an audio aggregation processing component that can aggregate the received data messages to assemble an audio recording, which can be used to support various downstream applications such as transcription.

In some embodiments, a method includes computer-implemented method for controlling a client device includes providing, from the client device to a computing system, a first notification that notifies the computing system that an audio data stream including a number of data messages has been initiated by the client device. The method further includes providing, from the client device to the computing system, a first data message including a first sequence number, a first timestamp, and a first payload, the first sequence number indicating a first position within the audio data stream to which the first payload corresponds. The method further includes storing, as a first buffered data message, the first data message in a buffer of the client device, the buffer including one or more buffered data messages. The method further includes determining that a first error condition for the first data message has occurred based on at least one of the one or more buffered data messages or a first acknowledgement status of the first data message. The method further includes, responsive to determining that the first error condition for the first data message has occurred, re-providing, from the client device to the computing system, the first data message.

In some embodiments, the audio data stream is associated with an in-progress audio recording being recording by the client device, in which the first payload includes a portion of the in-progress audio recording, in which the in-progress audio recording includes audio corresponding to a conversation involving a patient; and further including receiving, by the client device and from the computing system, a clinical note based on the conversation, the clinical note based on a transcript generated using the audio recording.

In some embodiments, providing the first notification to the computing system causes the computing system to initiate a process for generating an audio data file.

In some embodiments, determining the first error condition for the first data message includes determining an age for the first buffered data message based on the first timestamp, in which the age for the first buffered data message is based on a difference between a current time timestamp and the first timestamp and determining that the age for the first buffered data message exceeds a predetermined threshold.

In some embodiments, each buffered data message of the one or more buffered data messages has a respective timestamp. Determining the first error condition for the first data message includes determining the oldest buffered data message in the buffer based on the respective timestamps of the one or more buffered data messages, the oldest buffered data message including a timestamp of the oldest buffered data message and determining that the oldest buffered data message has an age exceeding a predetermined threshold, in which the age for the oldest buffered data message is based on a difference between a current time timestamp and the timestamp of the oldest buffered data message.

In some embodiments, determining the first error condition for the first data message includes determining that, after a predetermined period of time, the first acknowledgement status does not include receipt of an acknowledgement of the first data message.

In some embodiments, determining the first error condition for the first data message includes receiving a first indication that a network connection with the computing system is unavailable; receiving a second indication that the network connection with the computing system has become available following a period of unavailability; and determining, following the period of unavailability, that the first acknowledgement status does not include receipt of an acknowledgement of the first data message.

In some embodiments, the method further includes, after re-providing the first data message, providing, from the client device to the computing system, a second notification that notifies the computing system that the audio data stream has been terminated by the client device.

In some embodiments, the method further includes receiving, from the computing system, an acknowledgment of the first data message and, responsive to receiving the acknowledgement, remove the first data message from the buffer.

In some embodiments, the method further includes providing, from the client device to the computing system, a second data message including a second sequence number, a second timestamp, and a second payload, the second sequence number indicating a second position within the audio data stream to which the second payload corresponds, the second position being a position after the first position. The method further includes storing, as a second buffered data message, the second data message in the buffer. The method further includes providing, from the client device to the computing system, a third data message including a third sequence number, a third timestamp, and a third payload, the third sequence number indicating a third position within the audio data stream to which the third payload corresponds, the third position being a position after the first position. The method further includes storing, as a third buffered data message, the third data message in the buffer. The method further includes receiving, from the computing system, an acknowledgment of the second data message. The method further includes removing the second data message from the buffer.

In some embodiments, the first data message further includes a session identifier, the session identifier associated with a first session managed by the computing system; the audio data stream is associated with the first session; and the first session is associated with a number of client devices including the client device.

In some embodiments, the method further includes providing, from the client device to the computing system, a second data message including a second sequence number, a second timestamp, and a second payload, the second sequence number indicating a second position within the audio data stream to which the second payload corresponds, the second position being a position after the first position. The method further includes storing, as a second buffered data message, the second data message in the buffer. The method further includes providing, to the computing system, a second notification that notifies the computing system that the audio data stream has been terminated by the client device. The method further includes receiving, from the computing system after providing the second notification, an acknowledgment of the second data message. The method further includes removing the second data message from the buffer.

In some embodiments, the method further includes providing, from the client device to the computing system, a second data message including a second sequence number, a second timestamp, and a second payload, the second sequence number indicating a second position within the audio data stream to which the second payload corresponds, the second position being a position after the first position. The method further includes storing, as a second buffered data message, the second data message in the buffer. The method further includes providing, from the client device to the computing system, a third data message including a third sequence number, a third timestamp, and a third payload, the third sequence number indicating a third position within the audio data stream to which the third payload corresponds, the third position being a position after the second position. The method further includes storing, as a third buffered data message, the third data message in the buffer. The method further includes receiving, from the computing system, an acknowledgment of the third data message. The method further includes removing the third data message from the buffer.

In some embodiments, the method further includes providing, from the client device to the computing system, a second notification to pause the audio data stream including a second sequence number that is greater than the first sequence number and providing, from the client device to the computing system, a second data message including a third sequence number that is greater than the second sequence number, a second timestamp, and a second payload, the third sequence number indicating a second position within the audio data stream to which the second payload corresponds, the second position being a position after the first position.

In some embodiments, method further includes providing, from the client device to the computing system, a second notification to cancel the audio data stream and removing, from the buffer, all buffered data messages.

In some embodiments, a second method includes receiving, from the client device, the first notification that the audio data stream including the number of data messages has been initiated by the client device. The second method further includes receiving, from the client device, the first data message including the first sequence number, the first timestamp, and the first payload, the first sequence number indicating the first position within the audio data stream to which the first payload corresponds. The second method further includes storing first information about the first data message including the first sequence number and the first timestamp. The second method further includes storing the first data message using a storage system. The second method further includes providing, to the client device, a first acknowledgement of the first data message. The second method further includes receiving, from the client device, a second data message include a second sequence number, a second timestamp, and a second payload, the second sequence number indicating a second position within the audio data stream to which the second payload corresponds, the second position being a position after the first position. The second method further includes storing second information about the second data message including the second sequence number and the second timestamp. The second method further includes storing the second data message using the storage system. The second method further includes providing, to the client device, a second acknowledgement of the second data message. The second method further includes receiving, from the client device, a second notification that the audio data stream has been terminated by the client device. The second method further includes assembling an audio stream using the first data message and the second data message stored in the storage system using an ordering determined use the respective sequence numbers of the first data message and the second data message.

In some embodiments, the first data message and the second data message each include a portion of a streaming audio recording including one or more words spoken by a healthcare provider during a clinical encounter and the second method further includes outputting the audio stream to an ambient audio summary generation service including a transcription service and a clinical note generation service, in which the clinical note generation service is configured to generate a clinical note based on the clinical encounter using a transcript generated by the transcription service.

In some embodiments, the first sequence number of the first data message exceeds the second sequence number of the second data message.

In some embodiments, the second method further includes re-receiving, from the client device, the first data message. The second method further includes determining that the first data message has already been received. The second method further includes securely deleting the re-received first data message.

Some embodiments include a system that includes one or more processing systems and one or more computer-readable media storing instructions which, when executed by the one or more processing systems, cause the system to perform part or all of the operations and/or methods disclosed herein.

Some embodiments include one or more non-transitory computer-readable media storing instructions which, when executed by one or more processing systems, cause a system to perform part or all of the operations and/or methods disclosed herein.

The techniques described above and below may be implemented in a number of ways and in a number of contexts. Several example implementations and contexts are provided with reference to the following figures, as described below in more detail. However, the following implementations and contexts are but a few of many.

BRIEF DESCRIPTION OF THE DRAWINGS

Features, embodiments, and advantages of the present disclosure are better understood when the following Detailed Description is read with reference to the accompanying drawings.

DETAILED DESCRIPTION

Figure 1:
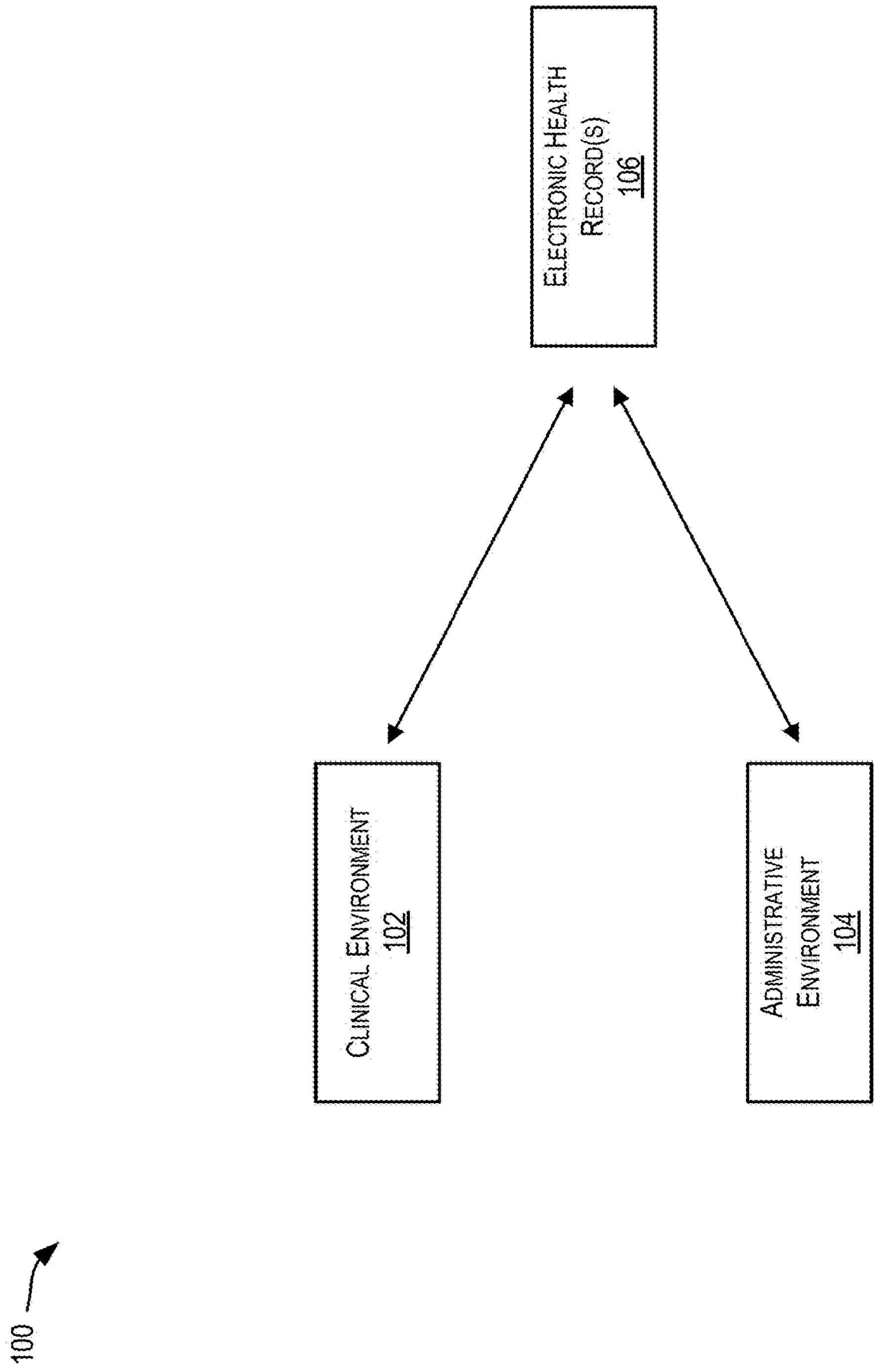
FIG. 1 shows an example of a healthcare environment, according to certain embodiments.

In the following description, for the purposes of explanation, specific details are set forth in order to provide a thorough understanding of certain embodiments. However, it will be apparent that various embodiments may be practiced without these specific details. The figures and description are not intended to be restrictive. The word "exemplary" is used herein to mean "serving as an example, instance, or illustration." Any embodiment or design described herein as "exemplary" is not necessarily to be construed as preferred or advantageous over other embodiments or designs.

As used herein, when an action is "based on" something, this means the action is based at least in part on at least a part of the something. As used herein, the terms "similarly," "substantially," "approximately" and "about" are defined as being largely but not necessarily wholly what is specified (and include wholly what is specified) as understood by one of ordinary skill in the art. In any disclosed embodiment, the term "similarly," "substantially," "approximately," or "about" may be substituted with "within [a percentage] of" what is specified, where the percentage includes 0.1, 1, 5, and 10 percent.

Overview

Sending audio data or other data over a network is often desired for applications in healthcare environments. For example, during a provider/patient encounter, a variety of data can be generated during the encounter. For instance, a digital assistant tool executing on a client device may be used to collect information about the patient encounter, as well as associated audio or video data. The resultant data can be sent to a remote server for additional processing either during the collection (e.g., "live-streamed" during the patient encounter as the audio data is being generated) or following the collection (e.g., streamed once the audio recording of the patient encounter is completed and saved to a file). For example, an audio recording of a patient encounter may be sent to a remote server where it can be used to generate a transcript of the encounter, which may then be used to generate a clinical note describing the encounter. The audio recording can likewise be used to populate the patient's chart, generate insurance or coding information, support telemedicine consultations, assist in medical education or training, provide data for clinical research or quality improvement initiatives, and so on. The audio recording may finally be persisted at the remote server for long-term storage or archiving.

To support these and other applications, the in-progress or completed audio recording (or other large data structure) can be sent over a network using various network protocols. In some examples, the audio or video data may be persisted locally as files on the client device following collection. The files can then be sent over the network to the remote server. In other examples, portions of the audio or video data can be temporarily stored in memory or on a filesystem of the client device and streamed to the remote server during collection.

In a healthcare scenario, compliance with certain regulatory regimes (e.g., the Health Insurance Portability and Accountability Act (HIPAA)) may involve restrictions on the amount of data that can be locally persisted during audio or video data collection. In these cases, the client device can be configured to only ephemerally persist or "buffer" the audio or video recording to a limited extent. The audio or video data then be sent or streamed as it is collected. In both cases, mechanisms or safeguards for ensuring the delivery and ordering of transmitted data are important for preserving the integrity of the collected data.

Streaming of a completed audio recording generally has various associated options to recover from errors that may occur during streaming because the source audio recording can be retained until it is fully transferred to the remote server. For example, if an unrecoverable error occurs during streaming, the file transfer can simply be restarted. However, error correction mechanisms such as resending entire files may be unusably slow for some applications. Moreover, streaming of completed audio recordings that are locally persisted may not comply with regulatory requirements such as the HIPAA regulations mentioned above. Certain regulations may specify that client devices not locally persist, for example, entire doctor patient conversations or encounters to any extent. The regulations may specify that client devices shall only buffer such conversations to a certain extent (e.g., a maximum amount of data or audio recording length) and not persist sensitive data locally. Consequently, live-streaming of an in-progress audio data collection during a patient encounter may be preferred.

However, existing approaches for sending an in-progress audio recording over a network present a number of challenges. Transmission of the audio recording as a continuous sequence of raw data is inefficient and multiplies the likelihood of error due to the multiplicity of transmissions. Consequently, the audio recording can be segmented and then sent over a network, one segment or portion at a time, as a data stream, where each segment includes a portion of the audio recording sized to optimize the amount of data sent with each transmission over the network. But this approach is ineffective when used without additional mechanisms for detecting, preventing, or correcting errors that may occur due to errors on the client device, remote server, network, or a combination thereof.

Existing approaches for sending an in-progress audio recording rely on error correction mechanisms that execute on the remote server. Such approaches may not be tolerant of out-of-order delivery of data messages that may commonly occur in some unreliable networks. For example, some existing approaches may use a "checksum" or other validation process to detect corrupted segments and request retransmission upon detection of an error. However, such approaches can introduce significant latency due to retransmission delays. Moreover, the client device may not store data that has already been sent over the network, which can preclude retransmission. This mechanism can be inefficient under high-loss conditions where multiple retransmissions or requests for retransmissions are may be needed, such as during a network outage. This approach also requires the remote server to continuously maintain records of the integrity of each data stream it is receiving, which may be impractical and computationally expensive in a production enterprise environment. Existing protocols may thus be unable to send data as it is being collected in real-time while also guaranteeing its delivery and order.

To address these challenges, techniques for data streaming and aggregation with client-initiated recovery are disclosed. In an example method provided to illustrate certain concepts, consider a client device used to record an audio recording of an encounter by a healthcare provider with a patient. During the encounter, the client device provides, to a remote server, a first notification that notifies the remote server that the client device is initiating an audio data stream including multiple data messages. The client device then begins sending the audio data stream by providing, to the remote server, a data message that includes a sequence number, a timestamp, and a payload. The payload may be, for example, a first, ordered segment of the audio recording. The sequence number, assigned to the data message by the client device, indicates the position of the payload within the audio data stream. For example, the data message may have the sequence number 1, indicating that it is the first portion of the audio recording. Subsequent data messages can contain subsequent portions. After providing the data message, the client device then stores a copy of the first message in a local buffer, such as an in-memory data structure or local filesystem. In this example, the data message is not locally persisted except for temporarily storing it in the buffer, as may be specified by certain regulatory regimes.

Under certain conditions, if no network or system errors intervene, the data message may be acknowledged by the remote server and can subsequently be deleted from the buffer. In this case, the data message can be considered successfully provided to the remote server. However, if a network or system error does occur, the client device determines an error condition associated with the data message based on information determined from the buffered data message or a lack of acknowledgement of receipt of the data message by the remote server. For example, the client device may determine, using the timestamp of the buffered data message, that no acknowledgement has been received from the remote server since the data message was provided 60 seconds ago. Responsive to determining that such an error condition exists, the client device re-provides the first data message to the remote server. This process can repeat, as needed, until an acknowledgement is received. In this example, the integrity of the audio recording is ensured by a client-initiated recovery mechanism that is effective independently of the status of the remote server or the network. Transmission of the data stream in this fashion can proceed for the duration of the in-progress audio recording. This example method thus additional, robust mechanisms for detecting, preventing, and correcting errors that may while streaming data. Furthermore, compliance with certain regulatory requirements is ensured by only storing the audio data messages in the buffer long enough to ensure delivery after which they are deleted.

Systems and methods according to the present disclosure provide significant improvements in the technical field of data streaming. In addition to overcoming the challenges outlined above, the techniques disclosed herein include a particular arrangement of components that together solve the technical problems exposed by existing approaches. Specifically, a client-side buffer along with a data stream coordinator that can identify error conditions during data streaming improve the existing approaches to data streaming that rely on protocols that are mediated by the remote server. Additionally, the techniques improve on existing approaches by tolerating out-of-order delivery of data messages that may commonly occur in some unreliable networks. The techniques can also provide a method for ensuring compliance with certain regulatory regimes by only maintaining ephemeral or buffered storage of sensitive information while simultaneously ensuring its delivery and order.

In addition, the techniques disclosed can improve the functioning of computers such as the client device and the remote server by reducing overall network traffic through needless retries and error handling, thereby reducing the overall computational load and computational resource consumption. For example, use of a client-side buffer reduces unnecessary duplication of network traffic by storing data locally and retransmitting only when error conditions or other continuity issues are identified, resulting in effective lower latency and faster recovery times. Because error handling and retransmission is allocated to the client device, server-side bottlenecks can be reduced while scalability for high-volume applications is improved.

These illustrative examples are given to introduce the reader to the general subject matter discussed herein and the disclosure is not limited to these examples. The following sections describe various additional non-limiting examples of systems and methods for data streaming and aggregation with client-initiated recovery.

Certain examples of this disclosure can be exemplified in the context of a healthcare environment. FIG. 1 shows an example of a healthcare environment 100, according to certain embodiments. Healthcare environment 100 can include a clinical environment 102 and an administrative environment 104. Clinical environment 102 represents a portion of the healthcare environment 100 involving the treatment, care, observation, and the like of patients. In a typical scenario, in the clinical environment 102, clinicians such as doctors and nurses can observe, treat, and care for patients and update the patients'electronic health records based on the observations, treatment, and care. In the clinical environment 102, clinicians can use electronic devices such as mobile phones, tablets, workstations, and computers to view, edit, and otherwise manage a patient's electronic health record, collect data during patient encounters, and to interact with various services that can consume data generated using the electronic devices. Administrative environment 104 represents a portion of the healthcare environment 100 involving the administration of the healthcare provider. For example, in the administrative environment 104, administrators such as records managers, front desk staff, secretaries can perform administrative tasks such as scheduling appointments, managing patient populations, providing customer service to facilitate operation of the healthcare environment 100. In the administrative environment 104, administrators can also use electronic devices such as mobile phones, tablets, workstations, and computer to view, edit, and otherwise manage electronic health records of patient population.

A patient can be associated with one or more electronic health records 106. Each electronic health record can be stored locally such as in a database or storage device managed by a healthcare provider and/or stored remotely such as in a cloud-based server or remote database managed by a service provider. Each electronic health record associated with a patient can be linked to other electronic health records associated with the patient. For example, one healthcare provider such as a family physician may generate an electronic health record for a patient and store that electronic health record in a local database and another healthcare provider such as a hospital may generate an electronic health record for the patient and store that electronic health record in a cloud-based databased. The two electronic health records for the patient can be linked to the patient using an identifier for the patient such as a portion of the patient's personally identifiable information.

In a healthcare setting or environment such as healthcare environment 100, dialog between entities is prevalent. For example, at any given moment, there could be dialog or conversation between patients and healthcare providers and between healthcare providers and administrators. In some cases, such dialog involves information regarding the care, treatment, observation, administration of a patient, and/or other information relevant to a patient's electronic health record. In some other cases, such dialog involves logistics of patient care such as what time is the physician's appointment, what operation the nurse is to perform, what information is relevant about the patient for the appointment, and the like. Healthcare providers and other providers have relied on various tools to facilitate care and management of patients in healthcare settings. In one example, microphones may be placed throughout a facility to record raw conversations from those in the facility and management software may be used to edit and organize those conversations such as providing dictations. These interactions can be recorded and persisted as audio recording that can be used for various downstream applications such as transcription, generation of clinical notes, subjection to additional analysis, and so on.

The healthcare environment 100 may further include AI-based applications. For example, healthcare providers can employ AI-based tools to facilitate care and management of their patient populations. In some cases, such AI-based tools can overcome certain challenges inherent to manual, traditional processes such as taking notes by hand. For example, a healthcare provider such as a pathologist may use an AI-based tool to predict a condition their patient may be afflicted with and automatically populate an electronic health record with the results. In another example, a radiologist may use an AI-based tool to automatically identify tumors and present results to the patient and/or a physician using an electronic health record. In a further example, a hospital may use an AI-based tool to identify predict a likelihood of disease for a portion of their patient population and automatically update administrative records accordingly.

CDAs (also referred to as clinical bots, chatbots, chatterbots, talkbots, skillbots) have become prevalent as of late. A digital assistant is an AI-based tool that can converse with end users. Generally, a digital assistant can respond to natural-language messages (e.g., questions or comments) provided by an end user using an application incorporates the bot. One example application is a messaging application in which natural-language messages are exchanged. End users interact with the digital assistant through conversational interactions (sometimes referred to as a conversational user interface (UI)), just as end users interact with other people. End users also interact with the bot through other types of interactions, such as transactional interactions (e.g., with a banking bot that is at least trained to transfer money from one account to another), informational interactions (e.g., with a human resources bot that is at least trained check the remaining vacation hours the user has), and/or retail interactions (e.g., with a retail bot that is at least trained for discussing returning purchased goods or seeking technical support). The data collected while using a CDA during, for example, a clinical encounter (e.g., audio data) can be captured and streamed to downstream services or servers for additional processing. As will be discussed further below, the techniques for data streaming and aggregation with client-initiated recovery disclosed herein can facilitate the streaming of such data.

Figure 2:
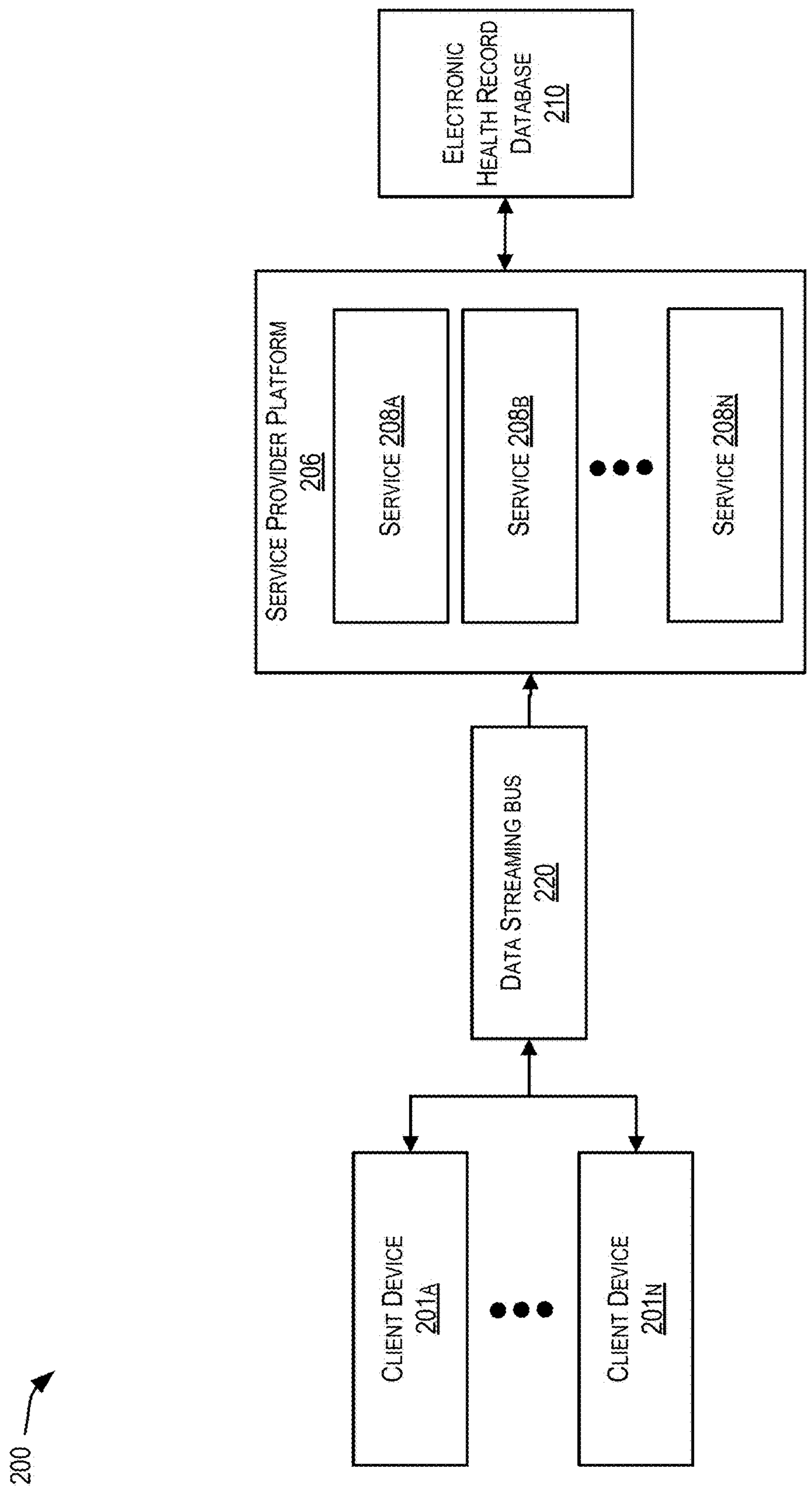
FIG. 2 shows an example artificial intelligence ("AI")-enabled system for providing a clinical digital assistant ("CDA"), according to certain embodiments.

FIG. 2 shows an example AI-enabled system 200 for providing a CDA, according to certain embodiments. The techniques for data streaming and aggregation with client-initiated recovery disclosed herein can be used to stream audio data gathered using the CDA to downstream services or servers for additional processing. As shown in FIG. 2, system 200 includes client devices 201A . . . N, a service provider platform 206, and electronic health record database 210. AI-enabled system 200 provides intelligent assistant services to healthcare providers such as doctors, nurses, technicians, clinicians, medical personnel, and the like. As used herein, the term healthcare provider generally refers to healthcare practitioners and professionals including, but not limited to: physicians (e.g., general practitioners, specialists, surgeons, etc.); nurse professionals (e.g., nurse practitioners, physician assistants, nursing staff, registered nurses, licensed practical nurses, etc.); other professionals (e.g., pharmacists, therapists, technicians, technologists, pathologists, dietitians, nutritionists, emergency medical technicians, psychiatrists, psychologists, counselors, dentists, orthodontists, hygienists, etc.).

The client devices 201A . . . N may include devices executing suitable client software such as mobile devices, tablets, laptop, desktops, smartwatches, and so on. Healthcare providers can interact with the client devices 201A . . . N based on touch input (e.g., tapping, swiping, pinching) and voice input captured by the electronic device, etc. Healthcare providers can use the client devices 201A . . . N to obtain information about a patient such as medical information from an electronic health record for the patient stored in the electronic health record database 210. Healthcare providers can also use the client devices 201A . . . N to collect information about a patient and information relevant to the observation, care, treatment, and/or management of a patient. Client devices 201A . . . N may include data collection capabilities including the capability to collect ambient sounds (natural and/or artificial) and information about events occurring in an environment in which the mobile application is located. Some client devices 201A . . . N can be used together to provide a multi-modal user experience. In other implementations, various client devices 201A . . . N can provide overlapping or different functions.

The client devices 201A . . . N can be connected to a service provider platform 206, via data streaming bus 220, which can provide assistant services to the client devices 201A . . . N. Services 208A . . . N can include, but are not limited to, authentication services, user management services, frontend services (e.g., entry point (facade) to all services), and other management services. Services 208A . . . N can also include, but are not limited to, ambient services (e.g., an AI-powered, voice-enabled service that automatically documents patient encounters accurately and efficiently at the point of care and provides quick action suggestions), dictation services (e.g., a service that allows doctors to generate medical records from voice e.g., using a Large Language Model ("LLM") or pre-seeded templates), digital assistant services (e.g., a server that allows you to create and deploy chatbots), speech services (e.g., an AI service that applies Automatic Speech Recognition ("ASR") technology to transform audio-based content into text). The client devices 201A . . . N along with the service provider platform 206 can enable clinicians to obtain information relevant to their patients (e.g., information in stored in electronic health record database 210) faster along with placing orders fasters (e.g., tests, medications, laboratories) all using a conversational experience (e.g., using one or more voice interfaces).

Multiplexed networked communication between the client devices 201A . . . N and the services 208A . . . N can present a formidable challenge, particularly at large scale. In a production setting, high-bandwidth, streaming data such as video or audio data may be sent continuously from the client devices 201A . . . N to multiple downstream consumer services 208A . . . N. In turn, the services 208A . . . N may be continuously sending responses back to the client devices 201A . . . N. For example, a particular client device (e.g., a smartphone) used for dictation may stream binary audio data to a storage service, an ASR service, and an audio processing service. The particular client device may, in turn, receive transcribed speech from the ASR service in near-real-time or with minimized latency.

A large healthcare organization (e.g., a large city hospital or geographically dispersed hospital system) may have thousands, tens of thousands, or hundreds of thousands—or even more—client devices being used simultaneously for healthcare delivery in various capacities. The relatively smaller number of services 208A . . . N may likewise be sending data back to the large number of client devices. Handling the routing of data at this scale can quickly become intractable. Consequently, some systems may include a messaging or stream orchestration layer such as the data streaming bus 220 in between the client devices 201A . . . N and the services 208A . . . N to coordinate the sending and receiving of streamed data.

The data streaming bus 220 includes components for receiving and routing messages to and from client devices to various backend services. The data streaming bus 220 can further include a session management component that can, for example, be used to ensure that messages are routed to all client devices in use by a particular user or users, thereby directing messages to multiple client devices for a single user or users using a specified route. The session management component can enable complex interactions between clients and services at the message routing layer rather than by application code.

Figure 3:
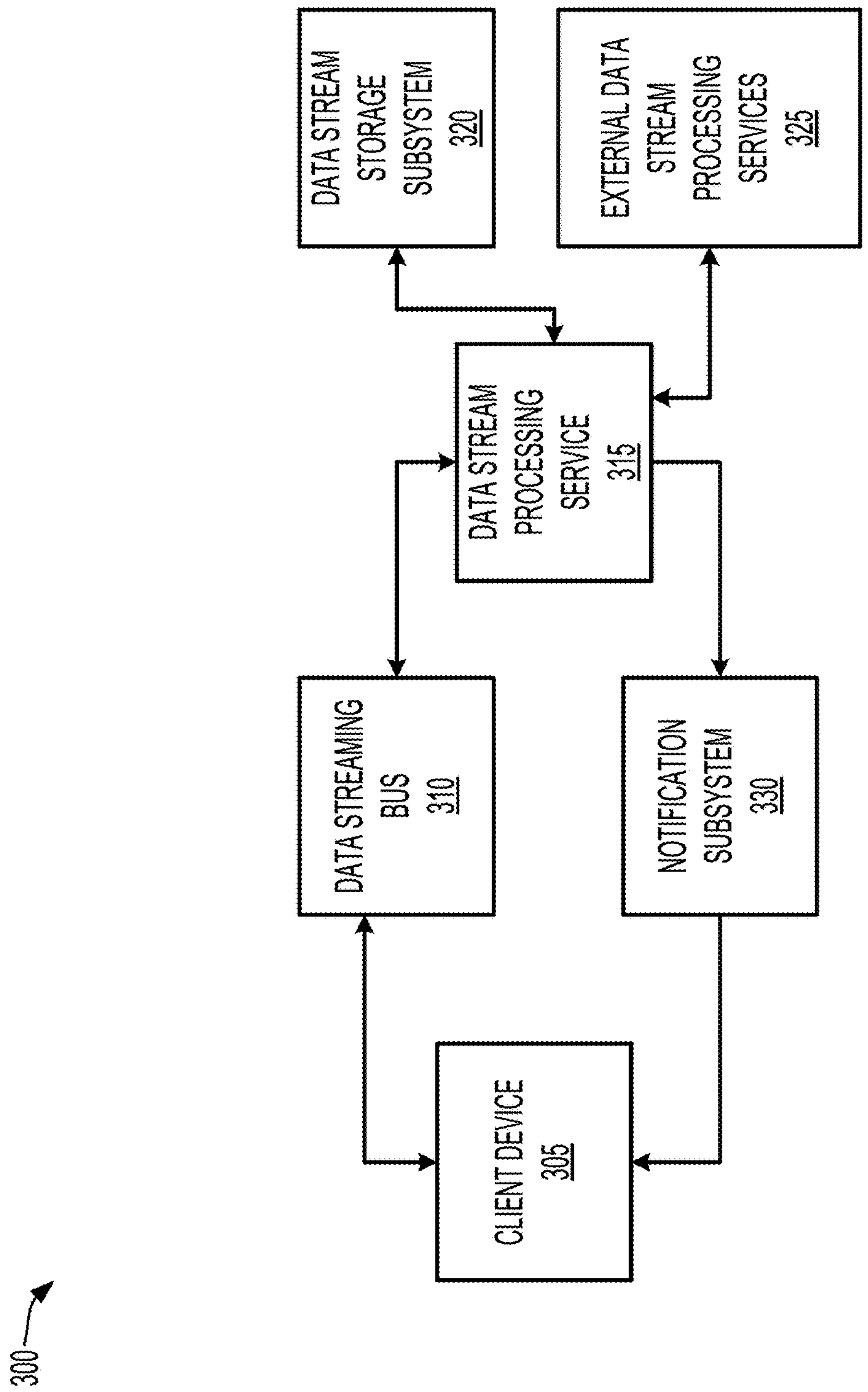
FIG. 3 depicts an example system for data streaming and aggregation with client-initiated recovery, according to certain embodiments.

FIG. 3 depicts an example system 300 for data streaming and aggregation with client-initiated recovery, according to certain embodiments. System 300 includes components for streaming data, such as a segmented audio recording, from one computing system to another. In this example, client device 305 streams data to a data stream processing service 335 via a data streaming bus 310. The client device 305 is communicatively coupled with the data stream processing service 335 over a network. The network may include the Internet, public networks, private networks, or combinations thereof.

The data streaming bus 310 can be used to provide flexible and efficient message routing between or the client device 305 and the data stream processing service 315 as part of a CDA backend implementation in the healthcare context as well as for many other applications. In some examples, the data streaming bus 310 can be configured to receive variable-length data messages and route them in accordance with routes specified using a custom polyglot stream orchestration language that can specify routes to and among various services and subsystems. The data streaming bus 310 can further provide session management for routing messages to groups of related consumers during the routing process, without the need for external session management by a standalone component or in the application layer.

The client device 305 can be any type of device capable of executing client software configured for data streaming such as a laptop, desktop, smartphone, tablet, internet protocol (IP) phones, and so on. For example, the client device 305 may be a smartphone or tablet executing software implementing CDA client software or other client software that includes facilities for capturing audio or other data (e.g., audio, video, etc.). The client device 305 can provide data messages to the data stream processing service 315 as a completed unit of data, or a portion thereof, or as an ongoing stream. For instance, the client device 305 can stream an audio recording, a portion of an in-progress audio recording, a live audio recording, and so on.

The data stream processing service 315 includes components for processing the streamed data messages. For example, streamed data messages can be aggregated to generate a file or another data stream. The aggregated data messages can then be used in conjunction with various downstream services and applications. The data stream processing service 335 can be a server or collection of servers, including a combination of privately or cloud-hosted devices. An example implementation of the data stream processing service 315 is shown below in FIG. 4. The data stream processing service 315 can communicate system state information (e.g., service status), information about events (e.g., completed transcription), and other relevant information to the client device 305 via the notification subsystem 330. The notification subsystem 330 can output messages to the client device 305 to cause alarms, alerts, push notifications, emails, text messages, and so on based on state or event information sent from the data stream processing service 315 as incoming data messages are processed.

The data stream processing service 315 may be communicatively coupled with a data stream storage subsystem 320. The data stream storage subsystem 320 can be used for temporary or persistent storage of received data messages, aggregated data messages (e.g., files or streams generated using received data messages), state information about received data streams, clients, overall system state information, and so on. The data stream storage subsystem 320 may include an in-memory cache, a filesystem, a database, or some combination thereof. For example, the data stream storage subsystem 320 may utilize an in-memory cache for low-latency input/output ("I/O") operations relating to data stream state, while using a database for persistent storage of aggregated data stored as files. The database may be, for example, a relational database management system (RDBMS) such as PostgreSQL or MySQL, configured to index and store the aggregated data and associated metadata.

The data stream processing service 315 may also be communicatively coupled with external data stream processing services 325 for processing of data messages and aggregated data messages. The data stream processing services 325 may include internally or externally hosted services accessed using a suitable programmatic or web-based (e.g., REST, SOAP, etc.) application programming interface ("API"). For example, in the healthcare context, the external data stream processing services 325 may include services for transcription, clinical note generation, storage, verification, and so on. However, the services included in the external data stream processing services 325 may vary in accordance with the particular constraints of the application supported by the data stream processing service 315.

It should be highlighted that while some examples of this disclosure are described in the healthcare context, the techniques for data streaming and aggregation with client-initiated recovery are applicable to any application in which a data stream including a number of data messages is streamed over a network from one computing system to another. For example, in addition to the healthcare context, the techniques can be applied in financial transaction processing, live video or audio streaming, real-time multiplayer gaming, and so on.

Figure 4:
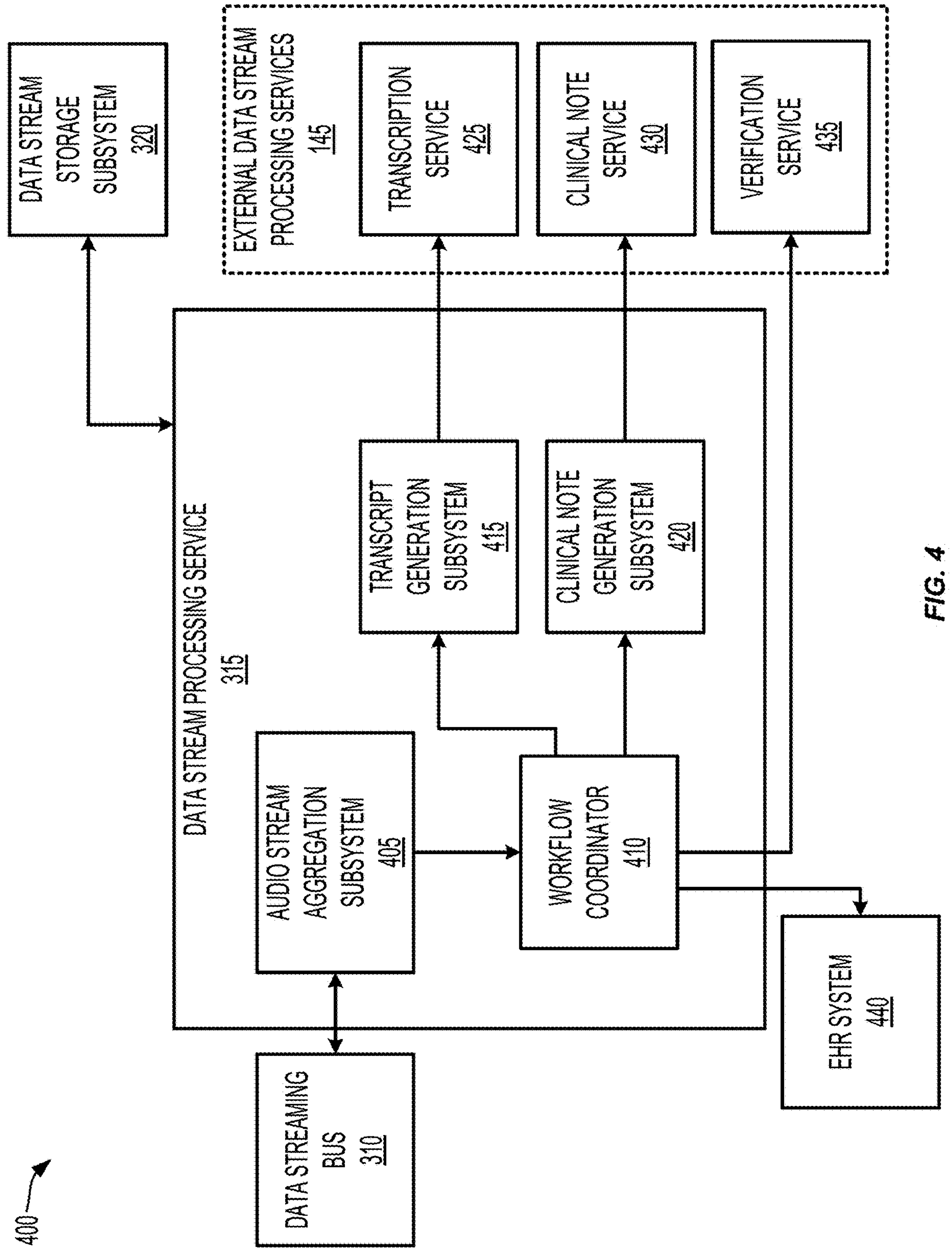
FIG. 4 depicts an example system for streaming and aggregation of ambient audio captured during an encounter between a healthcare provider and a patient, according to certain embodiments.

FIG. 4 depicts an example system 400 for streaming and aggregation of ambient audio captured during an encounter between a healthcare provider and a patient, according to certain embodiments. In some examples, a CDA can include functionality that captures and records ambient audio during an encounter between a healthcare provider and a patient. For instance, after a physician meets with a patient, the physician often manually produces a "clinical note" in a structured format (e.g., Subjective, Objective, Assessment, and Plan ("SOAP") notes) about the appointment. Traditionally, physicians would take notes by hand while meeting with patients and then, from those notes, manually create the clinical notes. The CDA may include an ambient audio capture service that can record the conversation between the physician and the patient, given explicit consent to do so from the patient. Then the CDA or an associated service can generate a draft clinical note for the physician for that appointment, thus freeing the physician from the time-consuming and error-prone burdens of taking notes and drafting the clinical note.

The ambient audio processing can be effected by the example implementation of the data stream processing service 315 shown in FIG. 4. Streaming audio data from an in-progress or completed audio recording can be received by an audio aggregation subsystem 405 by way of a data streaming bus 310, such as the example data streaming bus 310 described above with respect to FIG. 3. The audio aggregation subsystem 405 may be, for example, a software component of the data stream processing service 315 executing program code that can receive a segmented audio recording made up of a number of data messages and assemble the audio recording using an ordered sequence of the received data messages.

The received data messages, during aggregation, can be stored using the data stream storage subsystem 340, as described above with respect to FIG. 3. The assembled audio recording can likewise be stored using the data stream storage subsystem 340. Once the audio recording, or a portion thereof, is assembled, a workflow coordinator 410 can dispatch the audio recording to various subsystems or services, including external data steam processing services 345, according to the downstream applications configured. These subsystems or services can be used sequentially or in parallel, thus enabling the workflow coordinator 410 significant flexibility in processing of audio recordings and utilization of downstream resources. The external data steam processing services 345 are shown using a dashed line as a convenient grouping, but the services included therein may be hosted at disparate network locations.

The workflow coordinator 410 can be process automation software that manages and executes predefined workflows by coordinating data and task execution across multiple systems or components. The workflow coordinator 410 may include a workflow engine to control transitions, triggers, and notifications, etc. to manage sequencing and handling of predefined tasks such as transcription, verification, or clinical note generation, in the example healthcare context. In some examples, the workflow coordinator 410 may be alternatively implemented as a rules engine, state machine, event-driven processing framework, or other suitable approach.

In this example, the data stream processing service 315 includes a transcript generation subsystem 415 that can receive the audio recording, or a portion thereof. The transcript generation subsystem 415 can enqueue the audio recording with a transcription service 425 via an API such as a web-based REST API. The transcription service 425 may be hosted on another server, cloud provider, or may be a third-party service. The transcription service 425 can be configured to receive audio recordings, along with configuration information such as language, accuracy settings, context information (e.g., specifying the healthcare context), and so on. Following the availability of resources, the transcription service 425 can asynchronously generate a transcript of received audio recordings and relay them back to the transcript generation subsystem 415. The transcript generation subsystem 415 can store generated transcripts using the data stream storage subsystem 340.

The data stream processing service 315 also includes a clinical note generation subsystem 420 that can receive the audio recording, or a portion thereof, or a transcript of an audio recording previously generated and stored by the transcript generation subsystem 415. The clinical note generation subsystem 420 can enqueue the audio recording or transcript with a clinical note service 430 via an API such as a web-based REST API. The clinical note service 430 may be hosted on another server, cloud provider, or may be a third-party service. The clinical note service 430 can be configured to receive audio recordings or transcripts, along with configuration information such as note type (e.g., SOAP note), level of detail, specific provider or healthcare facility settings, and so on. Following the availability of resources, the clinical note service 430 can asynchronously generate a clinical note based on the received audio recordings or transcripts and relay it back to the clinical note generation subsystem 420. The clinical note generation subsystem 420 can store generated clinical notes using the data stream storage subsystem 340.

The workflow coordinator 410 can, following the generation of certain documents, output commands to cause the verification service 435 to enqueue a document for machine or human review. For example, the verification service 435 may be an external service that assigns documents to human reviewers or outputs documents to a machine learning model such as a large language model (e.g., GPT, Gemini, Claude, etc.) along with a suitable prompt. The human or machine reviewers can, for example, verify the accuracy of a transcription or clinical note, search for spelling, grammatical, or terminology errors, enforce compliance with organizational or regulatory requirements, and so on. Following the availability of resources and suitable time for review, the verification service 435 can asynchronously return information about the completed verification for each respective document, including an indication that the accuracy exceeds a predetermined threshold. In response, the workflow coordinator 410 can cause certain steps to be reperformed (e.g., a new transcript can be generated) or the document can be advanced to the new phase of processing.

The example data stream processing service 315 shown in FIG. 4 can be used to process an audio recording of a conversation between a physician and a patient to generate a draft clinical note. In this case, once the audio recording has completed during the patient encounter, the audio recording can be segmented and sent to the data stream processing service 315 using the methods disclosed herein. Once the data stream is complete, as signaled by the client device, the audio stream aggregation subsystem 405 assembles the segments into a complete audio stream or file and persists it using the data storage subsystem 140. The workflow coordinator 410 can then output a command to cause the transcript generation subsystem 415 to transcribe the audio recording. The workflow coordinator 410 can then output another command to cause a human evaluator to review the transcription for accuracy using the verification service 435. The workflow coordinator 410 can then output a command to cause the clinical note generation subsystem 420 to generate a draft clinical note using the generated transcript. Once again, the workflow coordinator 410 can output a command to cause a human evaluator to review the draft clinical note for accuracy using the verification service 435. Once accuracy of the clinical note has been verified, the workflow coordinate can output a command to cause a draft clinical note to be created in an electronic health records ("EHR") system 440 for the physician to review and approve. The EHR system can be configured to notify the physician that the draft clinical note is ready for review and approval, described in more detail in the next paragraph.

The system 400 also includes EHR system 440 that can be used by various components of the data stream processing engine 315 during audio recording processing and subsequent applications. The EHR system 440 can be accessed by the workflow coordinator and components of the data stream processing service using a suitable web-based API. For example, when generating a clinical note using the clinical note generation subsystem 420, the clinical note generation subsystem 420 can interact with EHR system 440 to retrieve past patient information (e.g., past conditions, current medications, etc.) to improve the accuracy and comprehensiveness of the generated clinical note for a particular patient. In another example, a generated clinical note can be uploaded to the EHR system 440, via the workflow coordinator 410, to require physician approval. The EHR system 440 can send a notification to the physician notifying them that the draft clinical note has been generated and uploaded the EHR system 440 and is ready for review/approval.

Figure 5:
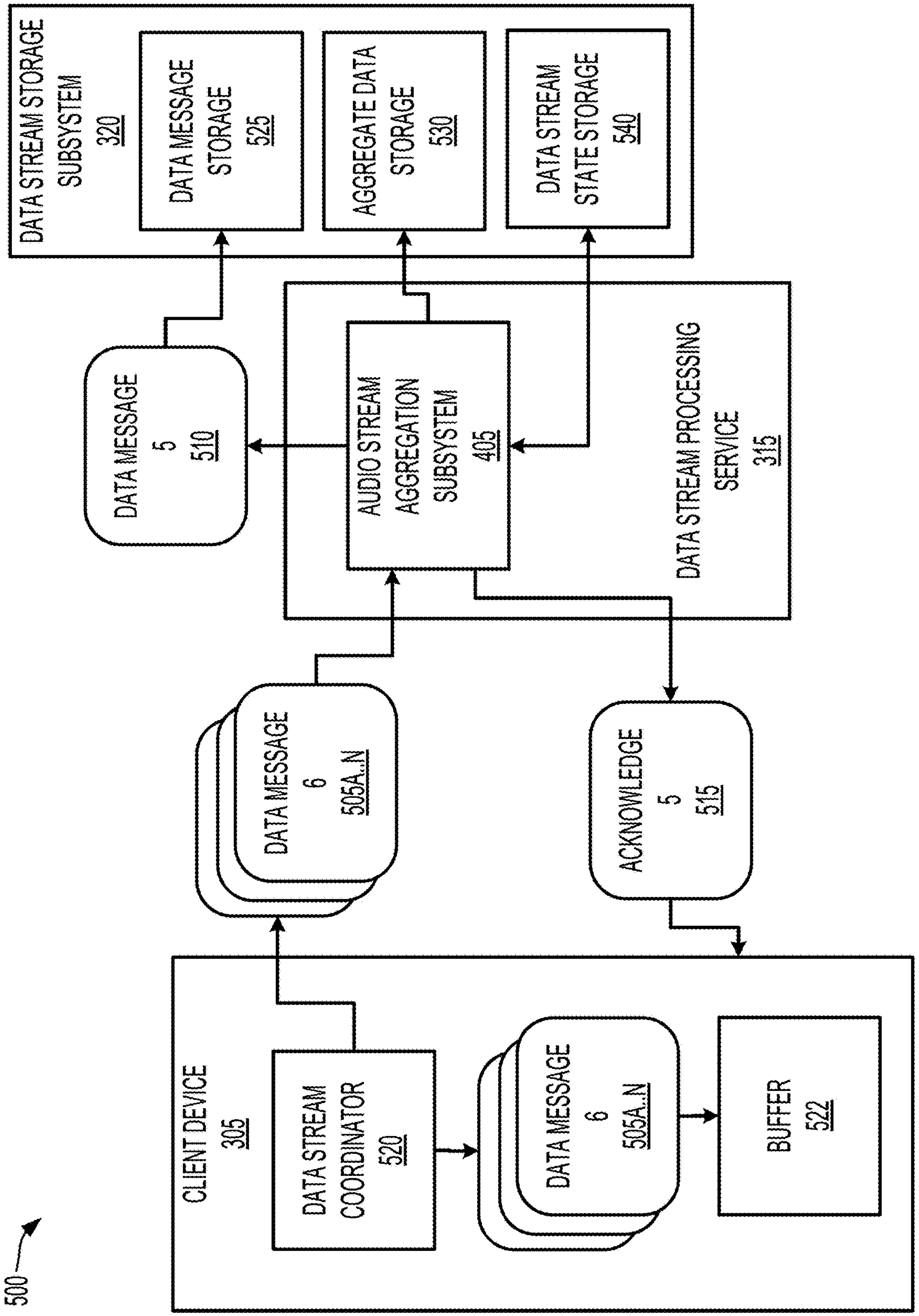
FIG. 5 depicts an example system for audio data streaming and aggregation with client-initiated recovery, according to certain embodiments.

FIG. 5 depicts an example system 500 for audio data streaming and aggregation with client-initiated recovery, according to certain embodiments. In this example, the client device 305 is used to capture ambient audio or to record audio. The captured audio is provided to the data stream processing service 315, which includes an audio stream aggregation subsystem 405, according to the example described above with respect to FIG. 4. The audio stream aggregation subsystem 405 can receive audio data messages from the client device 305 and aggregates them to generate an audio file. The system 500 depicts a snapshot in time during which data messages are provided to the data stream processing service 315, acknowledged, stored, and so on.

The client device 305 originates the data messages by segmenting or partitioning an audio recording into a number of data messages. The data messages may be from an in-progress (e.g., live-streamed) or completed audio recording. The client device 305 includes a data stream coordinator 520 that can receive the audio recording, or a portion thereof, and generate data streams, including a number of data messages, for provision to the data stream processing service 315. As data messages are provided to the data stream processing service 315, they are also ephemerally stored in buffer 522. The buffer 522 can store data messages from a number of different data streams. The buffer 522 may be an in-memory cache, file persisted on local or remote filesystem, data structure created programmatically, and so on. In system 500, the provision and storage of data messages 505A . . . N is depicted. Data messages 505A . . . N shows multiple data messages being provided simultaneously, exemplifying that encapsulation and temporary storage of the data messages 505A . . . N may involve more than one data message.

The generated data messages can be encapsulated into a suitable network protocol for provision to the data stream processing service 315. For example, data messages can be encapsulated into TCP segments including specification of a predefined port number for transmission to the data stream processing service 315. In another example, the data messages can be encapsulated within the body of an HTTP request (e.g., HTTP POST request) along with suitable headers specifying a content type such as application/octet-stream or MIME type and sent to a designated web-based API endpoint of the data stream processing service. Other protocols may be likewise used. The selected protocol or protocols may operate at the network layer, the transport layer, the application layer, or a combination thereof.

Data messages 505A . . . N also shows the sequence number 6 (only one sequence number is shown for visual clarity). The data messages 505A . . . N each include at least a sequence number, a timestamp (e.g., seconds since a predetermined epoch), and a payload (e.g., a portion of segment of an audio recording). The sequence number indicates a position within the audio data stream to which the corresponding payload corresponds. So, in an example where three data messages 505A . . . N are provided, they may have, respectively, the sequence numbers 6, 7, and 8.

Provided data messages are received at the audio stream aggregation subsystem 405, via a data streaming bus 310 (not shown). The audio stream aggregation subsystem 405 can acknowledge received data messages. Acknowledgement 515 depicts an acknowledgement of the data message having the sequence number 5. Client device 305 can receive acknowledgement 515 and remove the corresponding data message from the buffer 522 in response. It a data message is not acknowledged, a certain period of time elapses, or other condition is fulfilled, an error condition may be identified for that data message and the data message may be re-provided to the data stream processing service 315.

In addition to acknowledging received data messages, the audio stream aggregation subsystem 405 can temporarily store the data messages, prior to aggregation, as well as information about the various received data streams. In system 500, while also acknowledging it, the data message 510 with sequence number 5 is also stored at data message storage 525, a component of the data stream storage subsystem 320. The data message storage 525 may be, for example, an in-memory cache configured for efficient key-value-based storage and retrieval, since the data message 510 will typically only be stored as long as it takes to receive the segmented audio recording, or a portion thereof. In some examples, the data message storage 525 may be hosted using a cloud storage solution or other external server.

As received data messages are acknowledged and stored, information about each data stream being provided by each of a number of possible client devices can be stored at data stream state storage 540. The data stream state storage 540 may be, for example, an in-memory cache configured for key-value-based storage and retrieval, a relational database for long-term persistent storage, a filesystem, or other suitable storage media. The data stream state storage 540 can be used to store information about data streams such as the number of data messages received, sequence numbers, acknowledgements sent (or not yet sent), missing data messages, size, type, and so on. The persisted data stream state can be used, for example, to determine when a data stream is completed, or sufficiently completed, so that aggregation can begin. The persisted data stream state can be used to track the sending of acknowledgements, error conditions, resource consumption, and other aspects of audio stream reception and aggregation.

Once a data stream is complete, or partially complete, the audio stream aggregation subsystem 405 can aggregate the received data messages for a particular data stream and assemble them to generate an audio filed, including a header and other parts according to the particular file format. The ordering of the data messages can be determined using the sequence numbers. In some examples, generation of the audio file may involve "decoding" the audio data payloads within the data messages and arranging them in the correct sequence based on the sequence numbers. Generation of the audio file may further involve include adding appropriate metadata, such as headers and format-specific information, to ensure compliance with the specified file format. Decoding in this context can refer generally to converting the encoded audio data payloads from a compressed or encoded format into a raw or playable format suitable for assembly into the final audio file. The final audio file can be stored at the aggregate data storage component 530. The aggregate data storage 530 may be a database, such as a relational database or document store, which can be used to index and store the final, assembled audio file for later retrieval by downstream applications or services.

Figure 6:
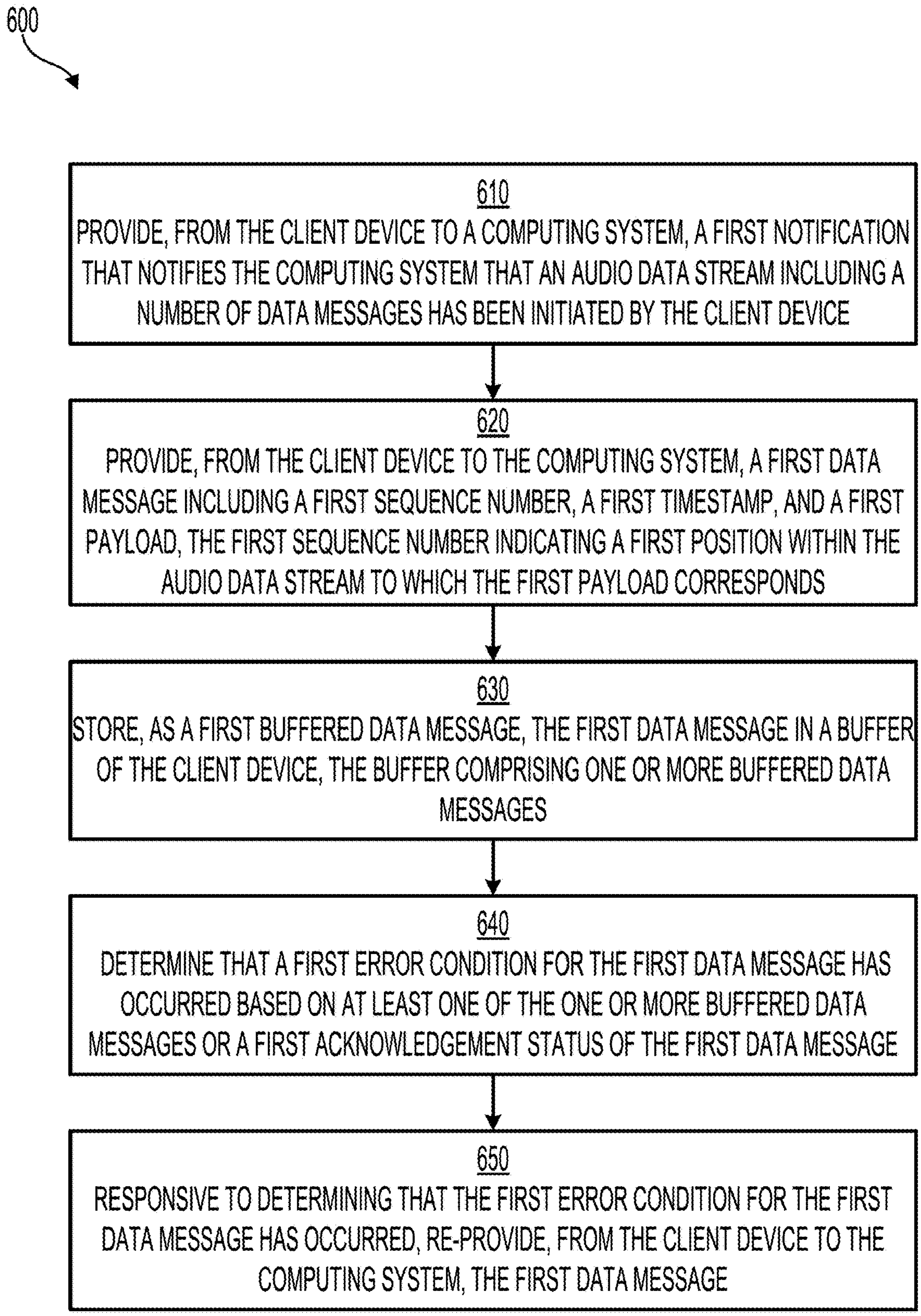
FIG. 6 depicts an example method for data streaming and aggregation with client-initiated recovery, according to some embodiments.

FIG. 6 depicts an example method 600 for data streaming and aggregation with client-initiated recovery, according to some embodiments. The description of the method 600 in FIG. 6 will be made with reference to FIGS. 3-5, however any suitable system according to this disclosure may be used. It should be appreciated that method 600 provides a particular method for providing data streaming and aggregation with client-initiated recovery. Other sequences of operations may also be performed according to alternative examples. For example, alternative examples of the present disclosure may perform the steps outlined below in a different order. Moreover, the individual operations illustrated by method 600 may include multiple sub-operations that may be performed in various sequences as appropriate to the individual operation. Furthermore, additional operations may be added or removed depending on the particular applications. Further, the operations described in method 600 may be performed by different devices. For example, the description is given from the perspective of the client device 305 but other configurations are possible. One of ordinary skill in the art would recognize many variations, modifications, and alternatives.

At block 610, a client device provides, to a computing system, a first notification that notifies the computing system that an audio data stream including a number of data messages has been initiated by the client device. For example, consider a client device such as a smartphone or tablet executing CDA client software used for collection of ambient audio information during a clinical encounter between a patient and a healthcare provider. During or following the conclusion of the encounter, the CDA client software may be configured to output the captured audio data to a remote server, such as the data stream processing service 315 described above. In this respect, the audio data stream can include data messages that are part of an ongoing audio recording (e.g., live-streaming). Compliance with certain regulatory regimes such as HIPAA may involve restrictions on the amount of data that can be locally persisted during audio or video data collection. In these cases, the audio or video data can then be sent or streamed as it is collected. In some other examples, the audio stream can be based on a completed audio recording (e.g., an audio file stored locally on the client device prior to streaming). In some examples, the audio data stream may be based on a pre-recorded audio recording which is now being streamed based on the availability of network resources.

As part of this transaction, the client device can notify the remote server that a data stream, such as an audio data stream, will commence. The audio data stream can be provided to the computing system to cause the computing system to generate an audio data file including a suitable header. The notification may include information about the audio data stream such as its type, size, security configuration, segmentation details, and so on. The notification may also include information about the protocol for streaming, such as this method 600, including information about how error conditions will be handled by the client device.

At block 620, the client device provides, to the computing system, a first data message including a first sequence number, a first timestamp, and a first payload, the first sequence number indicating a first position within the audio data stream to which the first payload corresponds. For example, the first data message may be provided to the computing system as a payload of a common networking protocol such as TCP/IP. In this example, the payload could be encapsulated within a TCP segment, which itself can be encapsulated within an IP packet for routing across the network. It should be emphasized that while this block uses the term "first data message," the word "first" is not meant to limit the described operation to the ordinally first data message in an audio data stream. The first data message can be the (ordinally) first or last data message in the audio data stream, as well as any data message between the (ordinally) first or last data message in the audio data stream.

In some examples, the first data message can include a portion of a streaming audio recording including one or more words spoken by a healthcare provider during a clinical encounter, as described above. For instance, the client device can partition or segment the completely or partially completed audio recording into a number of portions and the first data message can include the first such portion. In that case, the computing system may include one or more ambient audio summary generation services including a transcription service and a clinical note generation service such as the transcript generation subsystem 415 and the clinical note generation subsystem 420 described above with respect to FIG. 4. The clinical note generation service can, for example, generate a clinical note based on the clinical encounter using a transcript generated by the transcription service.

In addition to the contents listed above, the first data message may include other information. For example, the first data message may include a session identifier associated with a session managed by a component such as the data streaming bus 310. For instance, a session may be established for the healthcare encounter between the provider and patient which allows data to be streamed from the client device 305 to various backend services and then back to the particular client device 305. The data streaming bus 310 can use the session identifier to route data messages accordingly. In this respect, a particular audio stream can be associated with a particular session, which can in turn be associated with a number of different client devices and/or backend computing services.

In some examples, the data stream can be paused. For example, the client device can provide, to the computing system, a notification to pause the audio data stream including a sequence number that comes after the sequence number of the most recently sent data message. Then, the client device can provide, to the computing system, a next data message that includes a sequence number greater than the sequence number of the pause notification. In this example, the pause notification may be structurally similar to a data message and may be used to insert no audio or "whitespace" into an audio recording. For example, a pause notification may be equivalent to inserting a 2 second period of silence into the audio recording.

At block 630, the client device stores, as a first buffered data message, the first data message in a buffer of the client device, the buffer comprising one or more buffered data messages. For example, the buffer may be an in-memory cache, file persisted on local or remote filesystem, data structure created programmatically, and so on. The first data message can be copied and stored in the buffer, such that all of the information in the audio data message, including the first sequence number, the first timestamp, and the first payload can be used to re-instantiate and re-provide the first data message to the computing system in the event of an error condition. The buffered data message may be an exact duplicate of the first data message, or it may be a data structure populated with sufficient information to recreate the first data message at a later time.

At various times during audio streaming operations, the buffer may be empty, may stored one buffered data message, or may store any number of buffered data messages from any number of different audio data streams. In block 630, the buffer stores one or more buffered data messages as it is storing at least the first data message. It should be emphasized that while this block uses the term "first data message," the word "first" is not meant to limit the described operation to the ordinally first data message in an audio data stream. As described above, because the first data message can be the (ordinally) first, last, or intervening data message in the audio data stream, the one or more buffered data messages can accordingly store one or more (ordinally) first, last, or intervening data messages from a number of different audio data streams.

At block 640, the client device determines a first error condition for the first data message based on at least one of the one or more buffered data messages or a first acknowledgement status of the first data message. The first error condition may be caused by a network outage or slowdown, a system error associated with the remote computing system, or any other condition that results in a failure to receive an acknowledgement of the first data message from the computing system. The first error can be detected using a variety of techniques, a few examples of which are described below.

In some examples, determining the first error condition for the first data message can involve determining that the age of the first buffered data message based on the first timestamp exceeds a predetermined threshold. For instance, as described above, the buffered data message includes a timestamp that is associated with the time the first data message was initially provided to the computing system. The timestamp may be, for example, an "epoch" timestamp such as 1678886600, which represents the number of seconds that have elapsed since the beginning of a specified past time (e.g., Jan. 1, 1970, at 00:00:00 GMT)). The age of the first data message can be determined by, for example, subtracting the timestamp of the current client device system time from the timestamp associated with the first data message. The age thus computed can be compared with the predetermined threshold. An error condition can be identified if the age exceeds the predetermined threshold. The predetermined threshold can be configured based on the constraints of the particular application, network conditions, available computational resources and bandwidth, and so on. For instance, the predetermined threshold may be 5 seconds, 30 seconds, 1 minute, 5 minute, or other suitable value.

In some examples, determining the first error condition for the first data message can involve determining the oldest buffered data message in the buffer based on the respective timestamps of the one or more buffered data messages. As mentioned above, each buffered data message of the one or more buffered data messages has a respective timestamp. In this example, the timestamps of all of the buffered data messages can be compared to determine the oldest data message. For instance, the timestamps of the buffered data messages can be placed into a data structure such as an array and then sorted using an ascending order scheme. Then, the first member of the array, having the lowest timestamp, may be the oldest buffered data message. The error condition can then be determined by determining that the oldest buffered data message has an age exceeding a predetermined threshold. As above, the predetermined threshold can be configured based on the constraints of the particular application, network conditions, available computational resources and bandwidth, and so on. For instance, the predetermined threshold may be 5 seconds, 30 seconds, 1 minute, 5 minute, or other suitable value.

In addition to time-based methods, the error condition may be based on an acknowledgement status. An acknowledgement status can refer generally to factors such as whether an acknowledgement for a provided data message has been received, when it was received, what information was included in a received acknowledgement, and so on. the In some examples, determining the first error condition for the first data message can involve determining that, after a predetermined period of time, the first acknowledgement status does not include receipt of an acknowledgement of the first data message. In this example, the first acknowledgement status represents a lack of receipt of an acknowledgement for the first data message. The predetermined period of time can be configured based on the constraints of the particular application, network conditions, available computational resources and bandwidth, and so on. For instance, the predetermined period of time may be 5 seconds, 30 seconds, 1 minute, 5 minute, or other suitable value. Once the predetermined period of time has elapsed and the first acknowledgment status corresponds to a state of not having received an acknowledgement, an error condition may be determined to exist.

As mentioned above, determination of the first error condition may be based on other factors. In some examples, determining the first error condition for the first data message can involve first receiving am indication that a network connection with the computing system is unavailable. For example, provision of the first data message may fail with an error message or response that is indicative of an unavailable network connection. Later, a second indication that the network connection with the computing system has become available following a period of unavailability may be received. For example, where the HTTP protocol is in use, an HTTP request that previously timed out may receive a "200 OK" status code, indicating a successful connection and response from the server. Following this period of network unavailability, the client device can determine, following the period of unavailability, that the first acknowledgement status does not include receipt of an acknowledgement of the first data message. In other words, the client device can determine that an acknowledgement of the first data message may not have been received due to the network unavailability.

At block 650, the client device, responsive to determining the first error condition for the first data message, re-provides, to the computing system, the first data message. Upon identification of an error condition, the client device can recover from the error by providing the data message to the computing system again (as well as subsequent retries). Re-providing the first data message may be performed immediately upon identification of the error condition to minimize subsequent false positives for timing-based error condition identifications.

In some examples, after re-providing the first data message, the client device can provide, to the computing system, a second notification that notifies the computing system that the audio data stream is terminated. Following receipt of this, the computing system can assess the state of the received data messages and aggregate them according to, for example, their sequence numbers and other identifiers, to assemble an audio file. In some examples, the audio data stream may include multiple segmented audio recordings. In that case, the computing system can proceed to assemble each audio file when it determines that all information constituting the respective audio file has been received. For example, certain streamed data messages may include metadata that specify the number of data messages in the audio recording or the size of the audio recording. This information can be used to determine that all information for the respective audio file has been received and that aggregation can commence.

In some examples, acknowledgement of provided data messages may be received after the notification of termination has been sent. In that case, the acknowledged data message can be removed from the buffer to prevent re-provision of the data message, despite the terminated data stream. This can reduce unnecessary network traffic and reduce the computational load on the computing system. However, re-provision of buffered data messages can proceed even after the data stream is terminated. For example, the client device can determine that the age of a buffered data message has exceeded a predetermined threshold after the termination notification has been sent. In response to the age exceeding the predetermined threshold, the client device can re-provide, to the computing system, the first data message. In some examples, all buffered data messages associated with a terminated data stream may be removed upon acknowledgment of the termination notification.

In some examples, it may be desirable to cancel the data stream. For example, during a healthcare encounter, the encounter may be prematurely terminated, and the captured audio can be discarded. In this case, in response to a suitable selection using the client device user interface, the client device can provide, to the computing system, a notification to cancel the audio data stream. The computing system may, in response, take appropriate actions such as deleting any received data messages associated with the specified data stream and purging any persisted data stream state information. The client device can remove, from the buffer 522, all buffered data messages for the data stream.

In the absence of the error condition described above, the client device can receive, from the computing system, an acknowledgment of the first data message. In response to receiving the acknowledgement, the client device can remove the first data message from the buffer. For example, during normal operations in the absence of a network or server outage, each provided data message is promptly acknowledged within a short period of time (e.g., several hundred milliseconds or several seconds). Removal of the first data message from the buffer 522 may involve deleting it from buffer or archiving it using a soft deletion mechanism that retains the data for subsequent recovery if needed.

Receipt of acknowledgements and removal of buffered data messages need not necessarily correspond to the ordering or timing of provided data messages. For example, the client device can provide a second data message to the computing system and buffer the second data message. Then the client device can provide a third data message and buffer the third data message, before receiving an acknowledgement of the second data message. Then, the client device can receive, from the computing system, an acknowledgment of the second data message subsequently remove the second data message from the buffer 522. In this case, the third data message is provided before the second data message is acknowledged. In general, acknowledgments of data messages may be received at any time following the provision of those data messages, as long as the respective data stream has not been cancelled or terminated. For example, the client device can provide a second data message to the computing system and buffer the second data message. Then the client device can provide a third data message and buffer the third data message, before receiving an acknowledgement of the second data message. Then, the client device can receive, from the computing system, an acknowledgment of the third data message subsequently remove the third data message from the buffer 522, before the acknowledgement of the second data message has been received.

Figure 7A:
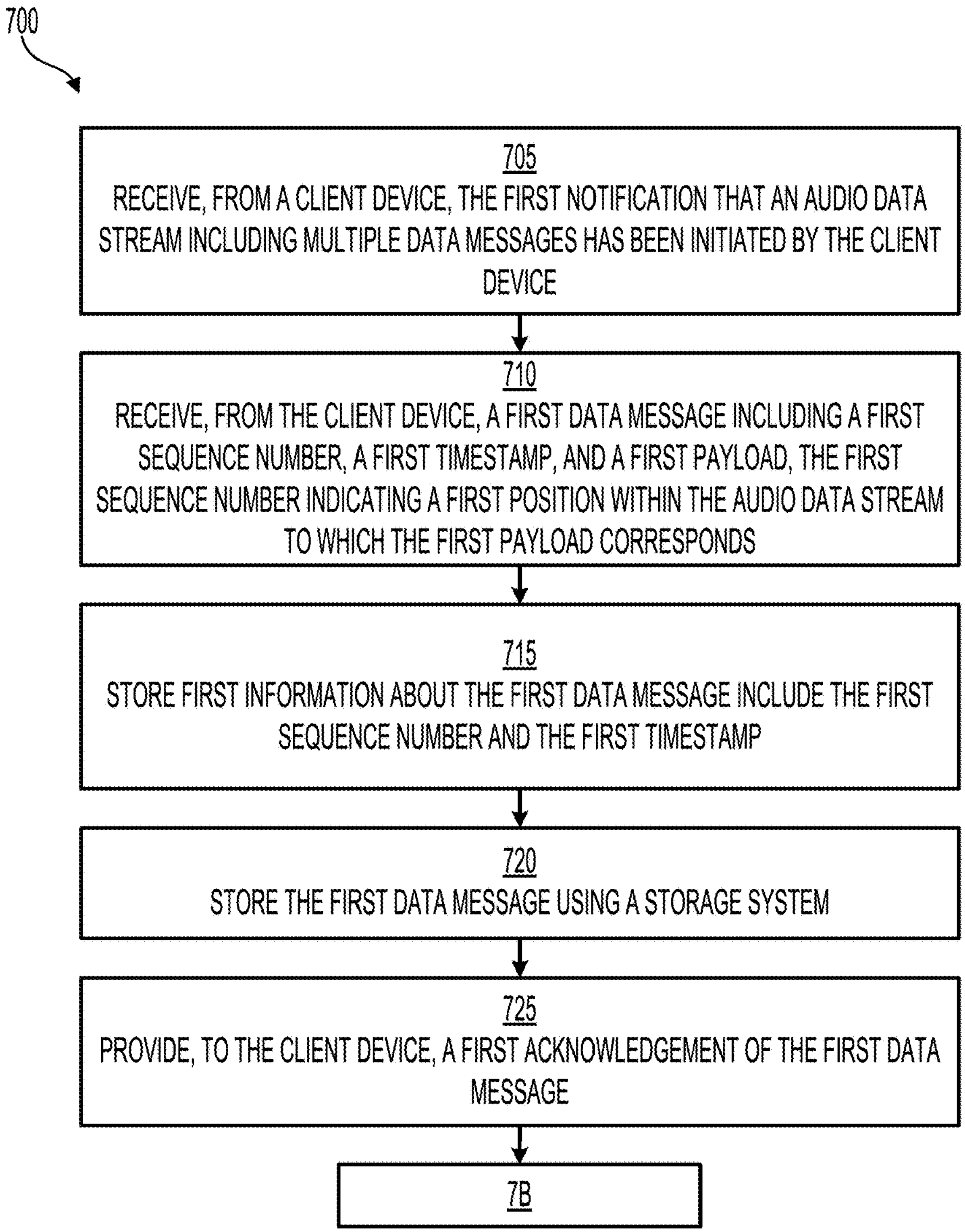
FIGS. 7A-7B depict another example method for data streaming and aggregation with client-initiated recovery, according to some embodiments.
Figure 7B:
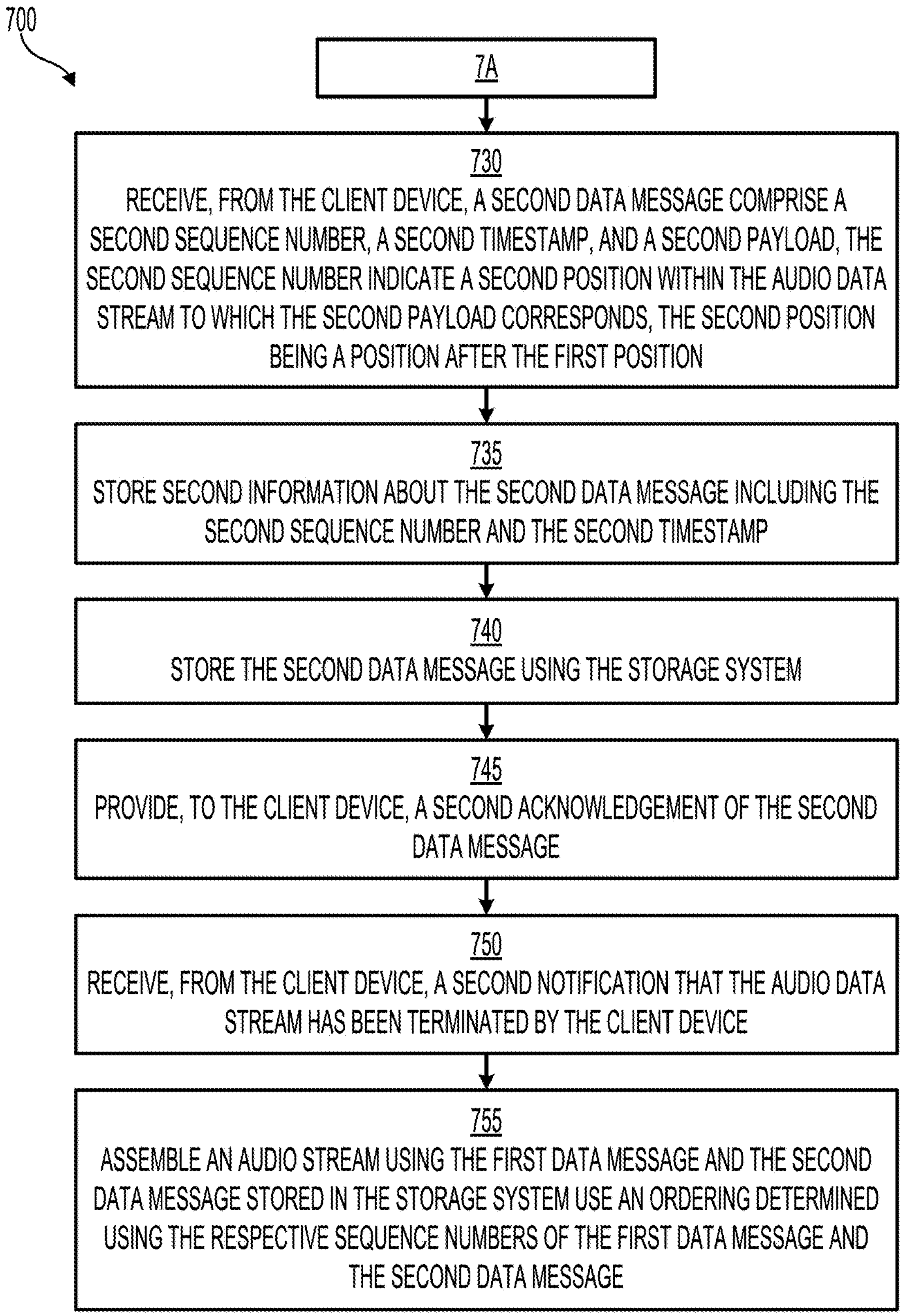

FIGS. 7A-7B depict another example method 700 for data streaming and aggregation with client-initiated recovery, according to some embodiments. The description of the method 700 in FIGS. 7A-7B will be made with reference to FIGS. 1-3, however any suitable system according to this disclosure may be used. It should be appreciated that method 700 provides a particular method for providing data streaming and aggregation with client-initiated recovery. Other sequences of operations may also be performed according to alternative examples. For example, alternative examples of the present disclosure may perform the steps outlined below in a different order. Moreover, the individual operations illustrated by method 700 may include multiple sub-operations that may be performed in various sequences as appropriate to the individual operation. Furthermore, additional operations may be added or removed depending on the particular applications. Further, the operations described in method 700 may be performed by different devices. For example, the description is given from the perspective of the data stream processing service 315 but other configurations are possible. One of ordinary skill in the art would recognize many variations, modifications, and alternatives.

At block 705, a computing system, such as the data stream processing service 315, receives, from a client device, a first notification that an audio data stream including a number of data messages has been initiated by the client device. For example, the first notification may be similar to the notification output by the client device as described above with respect to block 610 of FIG. 6. Compliance with certain regulatory regimes such as HIPAA may involve restrictions on the amount of data that can be locally persisted during audio or video data collection. In these cases, the data messages may be from audio can be streamed as it is collected and buffered on the client device long just enough to ensure delivery. Alternatively, the audio stream may be based on a just-completed or previously recorded audio recording. Following receipt of the first notification, the computing system can make certain preparations to receive the data stream including allocation of storage space in the data stream storage subsystem 320.

In some examples, the audio data stream may be associated with an identifier associated with the particular client device 305, user, healthcare provider, patient, etc. or a combination thereof. For example, the audio data stream may be associated with a particular session maintained by the data streaming bus 310. The session may be identified in the first notification (or subsequent data messages) by a session identifier included in the data message.

In some examples, receipt of the first notification can cause the computing system to initiate a process for generating an audio data file. For example, upon receipt of the first notification, the audio stream aggregation subsystem 405 can interface with the data stream storage subsystem 320 to allocate storage space for the expected data messages, aggregated data messages (e.g., files or streams generated using received data messages), state information about received data streams, and so on. The audio stream aggregation subsystem 405 can also allocate computational resources dedicated to the audio data stream, in whole or in part. For instance, certain process instantiations or memory allocations can be associated with the audio data stream for a particular client. In some examples, such allocations can be managed using the session, and associated facilities, described in the previous paragraph.

At block 710, the computing system receives, from the client device, a first data message including a first sequence number, a first timestamp, and a first payload, the first sequence number indicating a first position within the audio data stream to which the first payload corresponds. For example, the first data message may be similar to the first data message provided by the client device as described above with respect to block 620 of FIG. 6. It should be emphasized that while this block uses the term "first data message," the word "first" is not meant to limit the described operation to the ordinally first data message in an audio data stream. The first data message can be the (ordinally) first or last data message in the audio data stream, as well as any data message between the (ordinally) first or last data message in the audio data stream. The computing system can process the received first data message using the components of the data stream processing service 315 of FIG. 3.

At block 715, the computing system stores first information about the first data message including the first sequence number and the first timestamp. For example, the audio stream aggregation subsystem 405 (or similar component for other data stream types) can extract the components of the first data stream into a suitable data structure configured to contain the sequence number, payload, timestamp, etc. during processing. The first information including the first sequence number and the first timestamp can be ephemerally stored at the data stream state storage component 540, described above with respect to FIG. 5.

At block 720, the computing system stores the first data message using a storage system. For example, a copy (e.g., an exact duplicate) of the first data message can be stored at the data message storage component 525 or the elements of the first data message may be used to populate a data structure that can be used to recreate the first data message, again stored at the data message storage component 525.

At block 725, the computing system provides, to the client device, a first acknowledgement of the first data message. For example, once the components of the data stream storage subsystem 320 have returned positive confirmation of the storage of the first data message, its components, and its state (e.g., a "200 OK" response received from a web-based API), the computing system can generate an acknowledgment of the first data message. The generated acknowledgment may include identifying information about the first data message such as its timestamp or sequence number, as well as a checksum or hash to confirm integrity and ordering of the data message. The generated acknowledgment can be transmitted to the client device using a suitable network protocol, including as a response to the protocol used to send the first data message from the client device to the computing system. However, in some examples, the acknowledgement may be sent asynchronously after a short period of time (e.g., 10 milliseconds, 100 milliseconds, 1 second, 5 seconds, etc.).

At block 730, the computing system receives, from the client device, a second data message comprising a second sequence number, a second timestamp, and a second payload, the second sequence number indicating a second position within the audio data stream to which the second payload corresponds, the second position being a position after the first position. This block can proceed substantially as described above with respect to block 710. In some examples, the first sequence number of the first data message may exceed the second sequence number of the second data message. In other words, the data messages may be received by the computing system out of order. As is described in block 755 below, the computing system can assemble the audio file or stream irrespective of the order that the data messages are received by ordering the data messages according to their sequence numbers.

In some examples, identical data messages may be received multiple times. For example, client device may re-provide a data message after an acknowledgement has been sent, but before it has been received by the client device. In this case, the computing system can re-receive, from the client device, the data message. The computing system can determine that the first data message has already been received by, for example, comparing the received data message with messages or information stored in the data stream storage subsystem 320. The computing system can then securely deleting the re-received data message since it has been stored and is no longer needed.

At block 735, the computing system stores second information about the second data message including the second sequence number and the second timestamp. This block can proceed substantially as described above with respect to block 715.

At block 740, the computing system stores the second data message using the storage system. This block can proceed substantially as described above with respect to block 720.

At block 745, the computing system provides, to the client device, a second acknowledgement of the second data message. This block can proceed substantially as described above with respect to block 725.

At block 750, the computing system receives, from the client device, a second notification that the audio data stream has been terminated by the client device. For example, the second notification may be similar to the notification output by the client device as described above with respect to block 650 of FIG. 6. The second notification may include information indicating that the audio data stream is complete, its size, type, desired filetype, and other configuration information.

At block 755, the computing system assembles an audio stream using the first data message and the second data message stored in the storage system using an ordering determined use the respective sequence numbers of the first data message and the second data message. For example, the computing system can obtain the first and second data messages from the data stream storage subsystem 320 and identifies their respective sequence numbers to determine the correct order. The computing system can concatenate the data payloads from the first and second messages in the proper sequence for assembly. The system can then apply a specified decoding or transformation, to assemble a continuous audio stream or recording in the specified format.

For example, consider a first data message containing the payload for the first 1-second segment of audio and a second data message containing the payload for the next 1-second segment, for a 2-second audio recording. Both payloads may be stored in a particular audio format such as the MP3 format. The computing system can retrieve the two data messages, identify their sequence numbers (e.g., 1 and 2) to determine the order, and concatenate the MP3 data payloads in sequence. The computing system can validate the MP3 frames by checking synchronization bits, bitrate, sampling rate, and other header parameters for compliance and consistency. The computing system can then generate the MP3 file by combining the validated frames and adding metadata such as ID3 tags to store information such as the track title, artist, and album.

The data messages in method 700 can each include, for example, a portion of a streaming audio recording including one or more words spoken by a healthcare provider during a clinical encounter. The assembled audio stream can be output to an ambient audio summary generation service including a transcription service and a clinical note generation service, such as the transcript generation subsystem 415 and clinical note generation subsystem 420 of FIG. 4. For instance, the clinical note generation service may be configured to generate a clinical note based on the clinical encounter using a transcript generated by the transcription service.

Examples of Cloud Infrastructure

Some examples of the systems described above can be implemented as cloud computing or cloud-hosted systems. Infrastructure as a service (IaaS) is one particular type of cloud computing. IaaS can be configured to provide virtualized computing resources over a public network (e.g., the Internet). In an IaaS model, a cloud computing provider can host the infrastructure components (e.g., servers, storage devices, network nodes (e.g., hardware), deployment software, platform virtualization (e.g., a hypervisor layer), or the like). In some cases, an IaaS provider may also supply a variety of services to accompany those infrastructure components (example services include billing software, monitoring software, logging software, load balancing software, clustering software, etc.). Thus, as these services may be policy-driven, IaaS users may be able to implement policies to drive load balancing to maintain application availability and performance.

In some instances, IaaS customers may access resources and services through a wide area network (WAN), such as the Internet, and can use the cloud provider's services to install the remaining elements of an application stack. For example, the user can log in to the IaaS platform to create virtual machines (VMs), install operating systems (OSs) on each VM, deploy middleware such as databases, create storage buckets for workloads and backups, and even install enterprise software into that VM. Customers can then use the provider's services to perform various functions, including balancing network traffic, troubleshooting application issues, monitoring performance, managing disaster recovery, etc.

In most cases, a cloud computing model will require the participation of a cloud provider. The cloud provider may, but need not be, a third-party service that specializes in providing (e.g., offering, renting, selling) IaaS. An entity might also opt to deploy a private cloud, becoming its own provider of infrastructure services.

In some examples, IaaS deployment is the process of putting a new application, or a new version of an application, onto a prepared application server or the like. It may also include the process of preparing the server (e.g., installing libraries, daemons, etc.). This is often managed by the cloud provider, below the hypervisor layer (e.g., the servers, storage, network hardware, and virtualization). Thus, the customer may be responsible for handling (OS), middleware, and/or application deployment (e.g., on self-service virtual machines (e.g., that can be spun up on demand)) or the like.

In some examples, IaaS provisioning may refer to acquiring computers or virtual hosts for use, and even installing needed libraries or services on them. In most cases, deployment does not include provisioning, and the provisioning may need to be performed first.

In some cases, there are two different challenges for IaaS provisioning. First, there is the initial challenge of provisioning the initial set of infrastructure before anything is running. Second, there is the challenge of evolving the existing infrastructure (e.g., adding new services, changing services, removing services, etc.) once everything has been provisioned. In some cases, these two challenges may be addressed by enabling the configuration of the infrastructure to be defined declaratively. In other words, the infrastructure (e.g., what components are needed and how they interact) can be defined by one or more configuration files. Thus, the overall topology of the infrastructure (e.g., what resources depend on which, and how they each work together) can be described declaratively. In some instances, once the topology is defined, a workflow can be generated that creates and/or manages the different components described in the configuration files.

In some examples, an infrastructure may have many interconnected elements. For example, there may be one or more virtual private clouds (VPCs) (e.g., a potentially on-demand pool of configurable and/or shared computing resources), also known as a core network. In some examples, there may also be one or more inbound/outbound traffic group rules provisioned to define how the inbound and/or outbound traffic of the network will be set up and one or more virtual machines (VMs). Other infrastructure elements may also be provisioned, such as a load balancer, a database, or the like. As more and more infrastructure elements are desired and/or added, the infrastructure may incrementally evolve.

In some instances, continuous deployment techniques may be employed to enable deployment of infrastructure code across various virtual computing environments. Additionally, the described techniques can enable infrastructure management within these environments. In some examples, service teams can write code that is desired to be deployed to one or more, but often many, different production environments (e.g., across various different geographic locations, sometimes spanning the entire world). However, in some examples, the infrastructure on which the code will be deployed must first be set up. In some instances, the provisioning can be done manually, a provisioning tool may be utilized to provision the resources, and/or deployment tools may be utilized to deploy the code once the infrastructure is provisioned.

Figure 8:
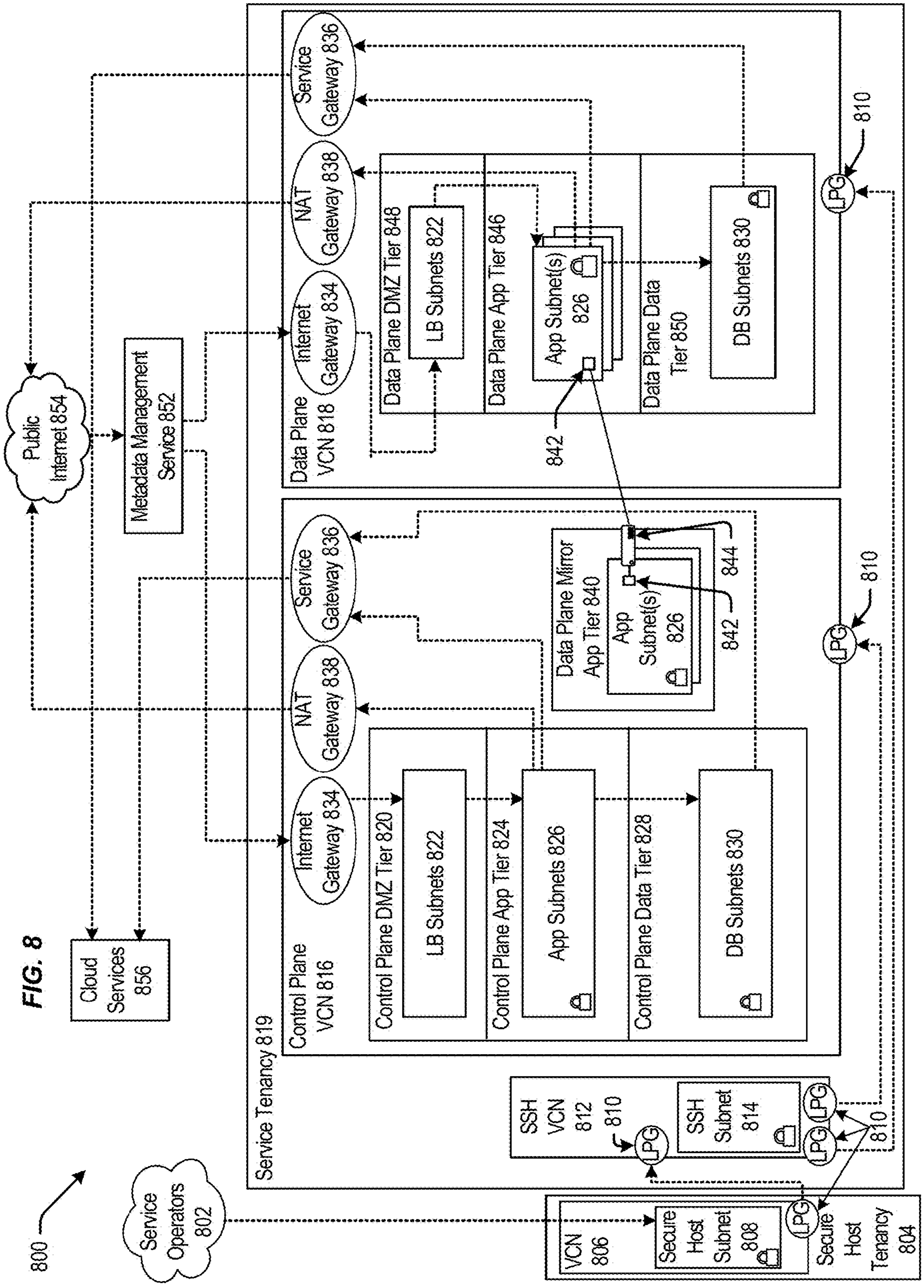
FIG. 8 is a block diagram illustrating one pattern for implementing a cloud infrastructure as a service system, according to at least one embodiment.

FIG. 8 is a block diagram 800 illustrating an example pattern of an IaaS architecture, according to at least one embodiment. Service operators 802 can be communicatively coupled to a secure host tenancy 804 that can include a virtual cloud network (VCN) 806 and a secure host subnet 808. In some examples, the service operators 802 may be using one or more client computing devices, which may be portable handheld devices (e.g., an iPhone®, cellular telephone, an iPad®, computing tablet, a personal digital assistant (PDA)) or wearable devices (e.g., a Google Glass® head mounted display), running software such as Microsoft Windows Mobile®, and/or a variety of mobile operating systems such as iOS, Windows Phone, Android, BlackBerry 8, Palm OS, and the like, and being Internet, e-mail, short message service (SMS), Blackberry®, or other communication protocol enabled. Alternatively, the client computing devices can be general purpose personal computers including, by way of example, personal computers and/or laptop computers running various versions of Microsoft Windows®, Apple Macintosh®, and/or Linux operating systems. The client computing devices can be workstation computers running any of a variety of commercially-available UNIX® or UNIX-like operating systems, including without limitation the variety of GNU/Linux operating systems, such as for example, Google Chrome OS. Alternatively, or in addition, client computing devices may be any other electronic device, such as a thin-client computer, an Internet-enabled gaming system (e.g., a Microsoft Xbox gaming console with or without a Kinect® gesture input device), and/or a personal messaging device, capable of communicating over a network that can access the VCN 806 and/or the Internet.

The VCN 806 can include a local peering gateway (LPG) 810 that can be communicatively coupled to a secure shell (SSH) VCN 812 via an LPG 810 contained in the SSH VCN 812. The SSH VCN 812 can include an SSH subnet 814, and the SSH VCN 812 can be communicatively coupled to a control plane VCN 816 via the LPG 810 contained in the control plane VCN 816. Also, the SSH VCN 812 can be communicatively coupled to a data plane VCN 818 via an LPG 810. The control plane VCN 816 and the data plane VCN 818 can be contained in a service tenancy 819 that can be owned and/or operated by the IaaS provider.

The control plane VCN 816 can include a control plane demilitarized zone (DMZ) tier 820 that acts as a perimeter network (e.g., portions of a corporate network between the corporate intranet and external networks). The DMZ-based servers may have restricted responsibilities and help keep breaches contained. Additionally, the DMZ tier 820 can include one or more load balancer (LB) subnet(s) 822, a control plane app tier 824 that can include app subnet(s) 826, a control plane data tier 828 that can include database (DB) subnet(s) 830 (e.g., frontend DB subnet(s) and/or backend DB subnet(s)). The LB subnet(s) 822 contained in the control plane DMZ tier 820 can be communicatively coupled to the app subnet(s) 826 contained in the control plane app tier 824 and an Internet gateway 834 that can be contained in the control plane VCN 816, and the app subnet(s) 826 can be communicatively coupled to the DB subnet(s) 830 contained in the control plane data tier 828 and a service gateway 836 and a network address translation (NAT) gateway 838. The control plane VCN 816 can include the service gateway 836 and the NAT gateway 838.

The control plane VCN 816 can include a data plane mirror app tier 840 that can include app subnet(s) 826. The app subnet(s) 826 contained in the data plane mirror app tier 840 can include a virtual network interface controller (VNIC) 842 that can execute a compute instance 844. The compute instance 844 can communicatively couple the app subnet(s) 826 of the data plane mirror app tier 840 to app subnet(s) 826 that can be contained in a data plane app tier 846.

The data plane VCN 818 can include the data plane app tier 846, a data plane DMZ tier 848, and a data plane data tier 850. The data plane DMZ tier 848 can include LB subnet(s) 822 that can be communicatively coupled to the app subnet(s) 826 of the data plane app tier 846 and the Internet gateway 834 of the data plane VCN 818. The app subnet(s) 826 can be communicatively coupled to the service gateway 836 of the data plane VCN 818 and the NAT gateway 838 of the data plane VCN 818. The data plane data tier 850 can also include the DB subnet(s) 830 that can be communicatively coupled to the app subnet(s) 826 of the data plane app tier 846.

The Internet gateway 834 of the control plane VCN 816 and of the data plane VCN 818 can be communicatively coupled to a metadata management service 852 that can be communicatively coupled to public Internet 854. Public Internet 854 can be communicatively coupled to the NAT gateway 838 of the control plane VCN 816 and of the data plane VCN 818. The service gateway 836 of the control plane VCN 816 and of the data plane VCN 818 can be communicatively coupled to cloud services 856.

In some examples, the service gateway 836 of the control plane VCN 816 or of the data plane VCN 818 can make application programming interface (API) calls to cloud services 856 without going through public Internet 854. The API calls to cloud services 856 from the service gateway 836 can be one-way: the service gateway 836 can make API calls to cloud services 856, and cloud services 856 can send requested data to the service gateway 836. But, cloud services 856 may not initiate API calls to the service gateway 836.

In some examples, the secure host tenancy 804 can be directly connected to the service tenancy 819, which may be otherwise isolated. The secure host subnet 808 can communicate with the SSH subnet 814 through an LPG 810 that may enable two-way communication over an otherwise isolated system. Connecting the secure host subnet 808 to the SSH subnet 814 may give the secure host subnet 808 access to other entities within the service tenancy 819.

The control plane VCN 816 may allow users of the service tenancy 819 to set up or otherwise provision desired resources. Desired resources provisioned in the control plane VCN 816 may be deployed or otherwise used in the data plane VCN 818. In some examples, the control plane VCN 816 can be isolated from the data plane VCN 818, and the data plane mirror app tier 840 of the control plane VCN 816 can communicate with the data plane app tier 846 of the data plane VCN 818 via VNICs 842 that can be contained in the data plane mirror app tier 840 and the data plane app tier 846.

In some examples, users of the system, or customers, can make requests, for example create, read, update, or delete (CRUD) operations, through public Internet 854 that can communicate the requests to the metadata management service 852. The metadata management service 852 can communicate the request to the control plane VCN 816 through the Internet gateway 834. The request can be received by the LB subnet(s) 822 contained in the control plane DMZ tier 820. The LB subnet(s) 822 may determine that the request is valid, and in response to this determination, the LB subnet(s) 822 can transmit the request to app subnet(s) 826 contained in the control plane app tier 824. If the request is validated and requires a call to public Internet 854, the call to public Internet 854 may be transmitted to the NAT gateway 838 that can make the call to public Internet 854. Metadata that may be desired to be stored by the request can be stored in the DB subnet(s) 830.

In some examples, the data plane mirror app tier 840 can facilitate direct communication between the control plane VCN 816 and the data plane VCN 818. For example, changes, updates, or other suitable modifications to configuration may be desired to be applied to the resources contained in the data plane VCN 818. Via a VNIC 842, the control plane VCN 816 can directly communicate with, and can thereby execute the changes, updates, or other suitable modifications to configuration to, resources contained in the data plane VCN 818.

In some embodiments, the control plane VCN 816 and the data plane VCN 818 can be contained in the service tenancy 819. In this case, the user, or the customer, of the system may not own or operate either the control plane VCN 816 or the data plane VCN 818. Instead, the IaaS provider may own or operate the control plane VCN 816 and the data plane VCN 818, both of which may be contained in the service tenancy 819. This embodiment can enable isolation of networks that may prevent users or customers from interacting with other users', or other customers', resources. Also, this embodiment may allow users or customers of the system to store databases privately without needing to rely on public Internet 854, which may not have a desired level of threat prevention, for storage.

In other embodiments, the LB subnet(s) 822 contained in the control plane VCN 816 can be configured to receive a signal from the service gateway 836. In this embodiment, the control plane VCN 816 and the data plane VCN 818 may be configured to be called by a customer of the IaaS provider without calling public Internet 854. Customers of the IaaS provider may desire this embodiment since database(s) that the customers use may be controlled by the IaaS provider and may be stored on the service tenancy 819, which may be isolated from public Internet 854.

Figure 9:
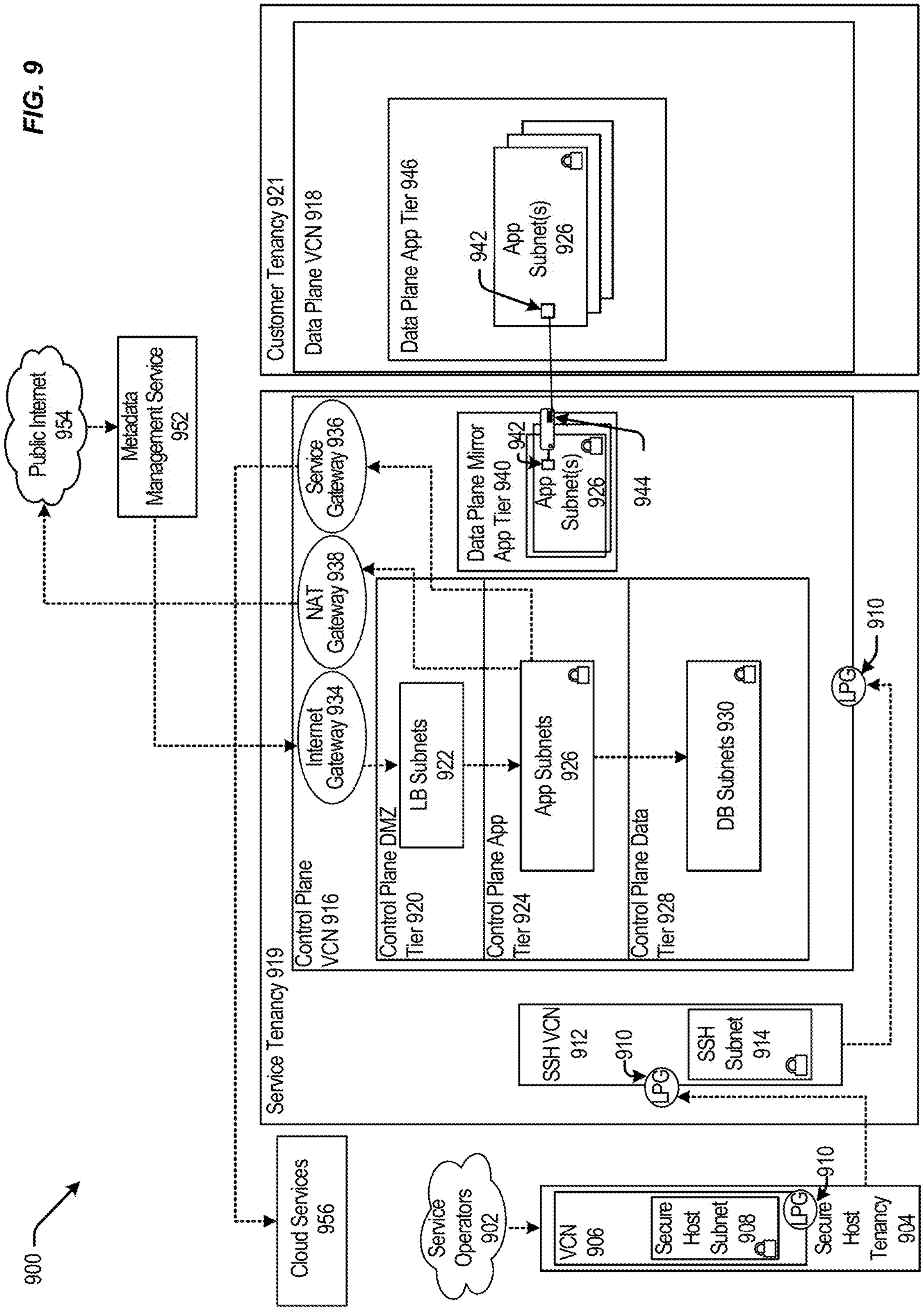
FIG. 9 is a block diagram illustrating another pattern for implementing a cloud infrastructure as a service system, according to at least one embodiment.

FIG. 9 is a block diagram 900 illustrating another example pattern of an IaaS architecture, according to at least one embodiment. Service operators 902 (e.g., service operators 802 of FIG. 8) can be communicatively coupled to a secure host tenancy 904 (e.g., the secure host tenancy 804 of FIG. 8) that can include a virtual cloud network (VCN) 906 (e.g., the VCN 806 of FIG. 8) and a secure host subnet 908 (e.g., the secure host subnet 808 of FIG. 8). The VCN 906 can include a local peering gateway (LPG) 910 (e.g., the LPG 810 of FIG. 8) that can be communicatively coupled to a secure shell (SSH) VCN 912 (e.g., the SSH VCN 812 of FIG. 8) via an LPG 810 contained in the SSH VCN 912. The SSH VCN 912 can include an SSH subnet 914 (e.g., the SSH subnet 814 of FIG. 8), and the SSH VCN 912 can be communicatively coupled to a control plane VCN 916 (e.g., the control plane VCN 816 of FIG. 8) via an LPG 910 contained in the control plane VCN 916. The control plane VCN 916 can be contained in a service tenancy 919 (e.g., the service tenancy 819 of FIG. 8), and the data plane VCN 918 (e.g., the data plane VCN 818 of FIG. 8) can be contained in a customer tenancy 921 that may be owned or operated by users, or customers, of the system.

The control plane VCN 916 can include a control plane DMZ tier 920 (e.g., the control plane DMZ tier 820 of FIG. 8) that can include LB subnet(s) 922 (e.g., LB subnet(s) 822 of FIG. 8), a control plane app tier 924 (e.g., the control plane app tier 824 of FIG. 8) that can include app subnet(s) 926 (e.g., app subnet(s) 826 of FIG. 8), a control plane data tier 928 (e.g., the control plane data tier 828 of FIG. 8) that can include database (DB) subnet(s) 930 (e.g., similar to DB subnet(s) 830 of FIG. 8). The LB subnet(s) 922 contained in the control plane DMZ tier 920 can be communicatively coupled to the app subnet(s) 926 contained in the control plane app tier 924 and an Internet gateway 934 (e.g., the Internet gateway 834 of FIG. 8) that can be contained in the control plane VCN 916, and the app subnet(s) 926 can be communicatively coupled to the DB subnet(s) 930 contained in the control plane data tier 928 and a service gateway 936 (e.g., the service gateway 836 of FIG. 8) and a network address translation (NAT) gateway 938 (e.g., the NAT gateway 838 of FIG. 8). The control plane VCN 916 can include the service gateway 936 and the NAT gateway 938.

The control plane VCN 916 can include a data plane mirror app tier 940 (e.g., the data plane mirror app tier 840 of FIG. 8) that can include app subnet(s) 926. The app subnet(s) 926 contained in the data plane mirror app tier 940 can include a virtual network interface controller (VNIC) 942 (e.g., the VNIC of 842) that can execute a compute instance 944 (e.g., similar to the compute instance 844 of FIG. 8). The compute instance 944 can facilitate communication between the app subnet(s) 926 of the data plane mirror app tier 940 and the app subnet(s) 926 that can be contained in a data plane app tier 946 (e.g., the data plane app tier 846 of FIG. 8) via the VNIC 942 contained in the data plane mirror app tier 940 and the VNIC 942 contained in the data plane app tier 946.

The Internet gateway 934 contained in the control plane VCN 916 can be communicatively coupled to a metadata management service 952 (e.g., the metadata management service 852 of FIG. 8) that can be communicatively coupled to public Internet 954 (e.g., public Internet 854 of FIG. 8). Public Internet 954 can be communicatively coupled to the NAT gateway 938 contained in the control plane VCN 916. The service gateway 936 contained in the control plane VCN 916 can be communicatively coupled to cloud services 956 (e.g., cloud services 856 of FIG. 8).

In some examples, the data plane VCN 918 can be contained in the customer tenancy 921. In this case, the IaaS provider may provide the control plane VCN 916 for each customer, and the IaaS provider may, for each customer, set up a unique compute instance 944 that is contained in the service tenancy 919. Each compute instance 944 may allow communication between the control plane VCN 916, contained in the service tenancy 919, and the data plane VCN 918 that is contained in the customer tenancy 921. The compute instance 944 may allow resources, that are provisioned in the control plane VCN 916 that is contained in the service tenancy 919, to be deployed or otherwise used in the data plane VCN 918 that is contained in the customer tenancy 921.

In other examples, the customer of the IaaS provider may have databases that live in the customer tenancy 921. In this example, the control plane VCN 916 can include the data plane mirror app tier 940 that can include app subnet(s) 926. The data plane mirror app tier 940 can reside in the data plane VCN 918, but the data plane mirror app tier 940 may not live in the data plane VCN 918. That is, the data plane mirror app tier 940 may have access to the customer tenancy 921, but the data plane mirror app tier 940 may not exist in the data plane VCN 918 or be owned or operated by the customer of the IaaS provider. The data plane mirror app tier 940 may be configured to make calls to the data plane VCN 918 but may not be configured to make calls to any entity contained in the control plane VCN 916. The customer may desire to deploy or otherwise use resources in the data plane VCN 918 that are provisioned in the control plane VCN 916, and the data plane mirror app tier 940 can facilitate the desired deployment, or other usage of resources, of the customer.

In some embodiments, the customer of the IaaS provider can apply filters to the data plane VCN 918. In this embodiment, the customer can determine what the data plane VCN 918 can access, and the customer may restrict access to public Internet 954 from the data plane VCN 918. The IaaS provider may not be able to apply filters or otherwise control access of the data plane VCN 918 to any outside networks or databases. Applying filters and controls by the customer onto the data plane VCN 918, contained in the customer tenancy 921, can help isolate the data plane VCN 918 from other customers and from public Internet 954.

In some embodiments, cloud services 956 can be called by the service gateway 936 to access services that may not exist on public Internet 954, on the control plane VCN 916, or on the data plane VCN 918. The connection between cloud services 956 and the control plane VCN 916 or the data plane VCN 918 may not be live or continuous. Cloud services 956 may exist on a different network owned or operated by the IaaS provider. Cloud services 956 may be configured to receive calls from the service gateway 936 and may be configured to not receive calls from public Internet 954. Some cloud services 956 may be isolated from other cloud services 956, and the control plane VCN 916 may be isolated from cloud services 956 that may not be in the same region as the control plane VCN 916. For example, the control plane VCN 916 may be located in "Region 1," and cloud service "Deployment 8," may be located in Region 1 and in "Region 2." If a call to Deployment 8 is made by the service gateway 936 contained in the control plane VCN 916 located in Region 1, the call may be transmitted to Deployment 8 in Region 1. In this example, the control plane VCN 916, or Deployment 8 in Region 1, may not be communicatively coupled to, or otherwise in communication with, Deployment 8 in Region 2.

Figure 10:
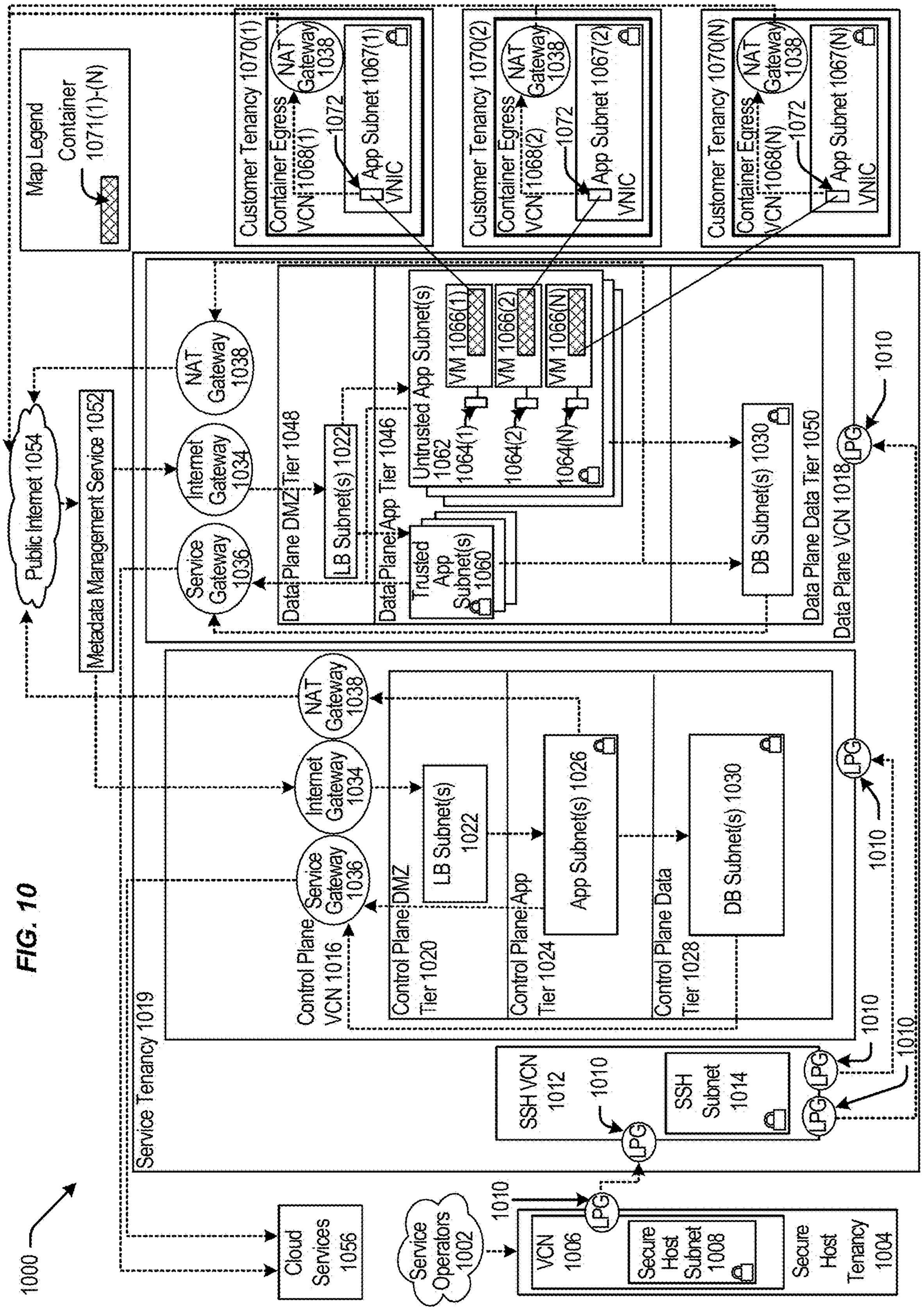
FIG. 10 is a block diagram illustrating another pattern for implementing a cloud infrastructure as a service system, according to at least one embodiment.

FIG. 10 is a block diagram 1000 illustrating another example pattern of an IaaS architecture, according to at least one embodiment. Service operators 1002 (e.g., service operators 802 of FIG. 8) can be communicatively coupled to a secure host tenancy 1004 (e.g., the secure host tenancy 804 of FIG. 8) that can include a virtual cloud network (VCN) 1006 (e.g., the VCN 806 of FIG. 8) and a secure host subnet 1008 (e.g., the secure host subnet 808 of FIG. 8). The VCN 1006 can include an LPG 1010 (e.g., the LPG 810 of FIG. 8) that can be communicatively coupled to an SSH VCN 1012 (e.g., the SSH VCN 812 of FIG. 8) via an LPG 1010 contained in the SSH VCN 1012. The SSH VCN 1012 can include an SSH subnet 1014 (e.g., the SSH subnet 814 of FIG. 8), and the SSH VCN 1012 can be communicatively coupled to a control plane VCN 1016 (e.g., the control plane VCN 816 of FIG. 8) via an LPG 1010 contained in the control plane VCN 1016 and to a data plane VCN 1018 (e.g., the data plane 818 of FIG. 8) via an LPG 1010 contained in the data plane VCN 1018. The control plane VCN 1016 and the data plane VCN 1018 can be contained in a service tenancy 1019 (e.g., the service tenancy 819 of FIG. 8).

The control plane VCN 1016 can include a control plane DMZ tier 1020 (e.g., the control plane DMZ tier 820 of FIG. 8) that can include load balancer (LB) subnet(s) 1022 (e.g., LB subnet(s) 822 of FIG. 8), a control plane app tier 1024 (e.g., the control plane app tier 824 of FIG. 8) that can include app subnet(s) 1026 (e.g., similar to app subnet(s) 826 of FIG. 8), a control plane data tier 1028 (e.g., the control plane data tier 828 of FIG. 8) that can include DB subnet(s) 1030. The LB subnet(s) 1022 contained in the control plane DMZ tier 1020 can be communicatively coupled to the app subnet(s) 1026 contained in the control plane app tier 1024 and to an Internet gateway 1034 (e.g., the Internet gateway 834 of FIG. 8) that can be contained in the control plane VCN 1016, and the app subnet(s) 1026 can be communicatively coupled to the DB subnet(s) 1030 contained in the control plane data tier 1028 and to a service gateway 1036 (e.g., the service gateway of FIG. 8) and a network address translation (NAT) gateway 1038 (e.g., the NAT gateway 838 of FIG. 8). The control plane VCN 1016 can include the service gateway 1036 and the NAT gateway 1038.

The data plane VCN 1018 can include a data plane app tier 1046 (e.g., the data plane app tier 846 of FIG. 8), a data plane DMZ tier 1048 (e.g., the data plane DMZ tier 848 of FIG. 8), and a data plane data tier 1050 (e.g., the data plane data tier 850 of FIG. 8). The data plane DMZ tier 1048 can include LB subnet(s) 1022 that can be communicatively coupled to trusted app subnet(s) 1060 and untrusted app subnet(s) 1062 of the data plane app tier 1046 and the Internet gateway 1034 contained in the data plane VCN 1018. The trusted app subnet(s) 1060 can be communicatively coupled to the service gateway 1036 contained in the data plane VCN 1018, the NAT gateway 1038 contained in the data plane VCN 1018, and DB subnet(s) 1030 contained in the data plane data tier 1050. The untrusted app subnet(s) 1062 can be communicatively coupled to the service gateway 1036 contained in the data plane VCN 1018 and DB subnet(s) 1030 contained in the data plane data tier 1050. The data plane data tier 1050 can include DB subnet(s) 1030 that can be communicatively coupled to the service gateway 1036 contained in the data plane VCN 1018.

The untrusted app subnet(s) 1062 can include one or more primary VNICs 1064(1)-(N) that can be communicatively coupled to tenant virtual machines (VMs) 1066(1)-(N). Each tenant VM 1066(1)-(N) can be communicatively coupled to a respective app subnet 1067(1)-(N) that can be contained in respective container egress VCNs 1068(1)-(N) that can be contained in respective customer tenancies 1070(1)-(N). Respective secondary VNICs 1072(1)-(N) can facilitate communication between the untrusted app subnet(s) 1062 contained in the data plane VCN 1018 and the app subnet contained in the container egress VCNs 1068(1)-(N). Each container egress VCNs 1068(1)-(N) can include a NAT gateway 1038 that can be communicatively coupled to public Internet 1054 (e.g., public Internet 854 of FIG. 8).

The Internet gateway 1034 contained in the control plane VCN 1016 and contained in the data plane VCN 1018 can be communicatively coupled to a metadata management service 1052 (e.g., the metadata management system 852 of FIG. 8) that can be communicatively coupled to public Internet 1054. Public Internet 1054 can be communicatively coupled to the NAT gateway 1038 contained in the control plane VCN 1016 and contained in the data plane VCN 1018. The service gateway 1036 contained in the control plane VCN 1016 and contained in the data plane VCN 1018 can be communicatively coupled to cloud services 1056.

In some embodiments, the data plane VCN 1018 can be integrated with customer tenancies 1070. This integration can be useful or desirable for customers of the IaaS provider in some cases such as a case that may desire support when executing code. The customer may provide code to run that may be destructive, may communicate with other customer resources, or may otherwise cause undesirable effects. In response to this, the IaaS provider may determine whether to run code given to the IaaS provider by the customer.

In some examples, the customer of the IaaS provider may grant temporary network access to the IaaS provider and request a function to be attached to the data plane app tier 1046. Code to run the function may be executed in the VMs 1066(1)-(N), and the code may not be configured to run anywhere else on the data plane VCN 1018. Each VM 1066(1)-(N) may be connected to one customer tenancy 1070. Respective containers 1071(1)-(N) contained in the VMs 1066(1)-(N) may be configured to run the code. In this case, there can be a dual isolation (e.g., the containers 1071(1)-(N) running code, where the containers 1071(1)-(N) may be contained in at least the VM 1066(1)-(N) that are contained in the untrusted app subnet(s) 1062), which may help prevent incorrect or otherwise undesirable code from damaging the network of the IaaS provider or from damaging a network of a different customer. The containers 1071(1)-(N) may be communicatively coupled to the customer tenancy 1070 and may be configured to transmit or receive data from the customer tenancy 1070. The containers 1071(1)-(N) may not be configured to transmit or receive data from any other entity in the data plane VCN 1018. Upon completion of running the code, the IaaS provider may kill or otherwise dispose of the containers 1071(1)-(N).

In some embodiments, the trusted app subnet(s) 1060 may run code that may be owned or operated by the IaaS provider. In this embodiment, the trusted app subnet(s) 1060 may be communicatively coupled to the DB subnet(s) 1030 and be configured to execute CRUD operations in the DB subnet(s) 1030. The untrusted app subnet(s) 1062 may be communicatively coupled to the DB subnet(s) 1030, but in this embodiment, the untrusted app subnet(s) may be configured to execute read operations in the DB subnet(s) 1030. The containers 1071(1)-(N) that can be contained in the VM 1066(1)-(N) of each customer and that may run code from the customer may not be communicatively coupled with the DB subnet(s) 1030.

In other embodiments, the control plane VCN 1016 and the data plane VCN 1018 may not be directly communicatively coupled. In this embodiment, there may be no direct communication between the control plane VCN 1016 and the data plane VCN 1018. However, communication can occur indirectly through at least one method. An LPG 1010 may be established by the IaaS provider that can facilitate communication between the control plane VCN 1016 and the data plane VCN 1018. In another example, the control plane VCN 1016 or the data plane VCN 1018 can make a call to cloud services 1056 via the service gateway 1036. For example, a call to cloud services 1056 from the control plane VCN 1016 can include a request for a service that can communicate with the data plane VCN 1018.

Figure 11:
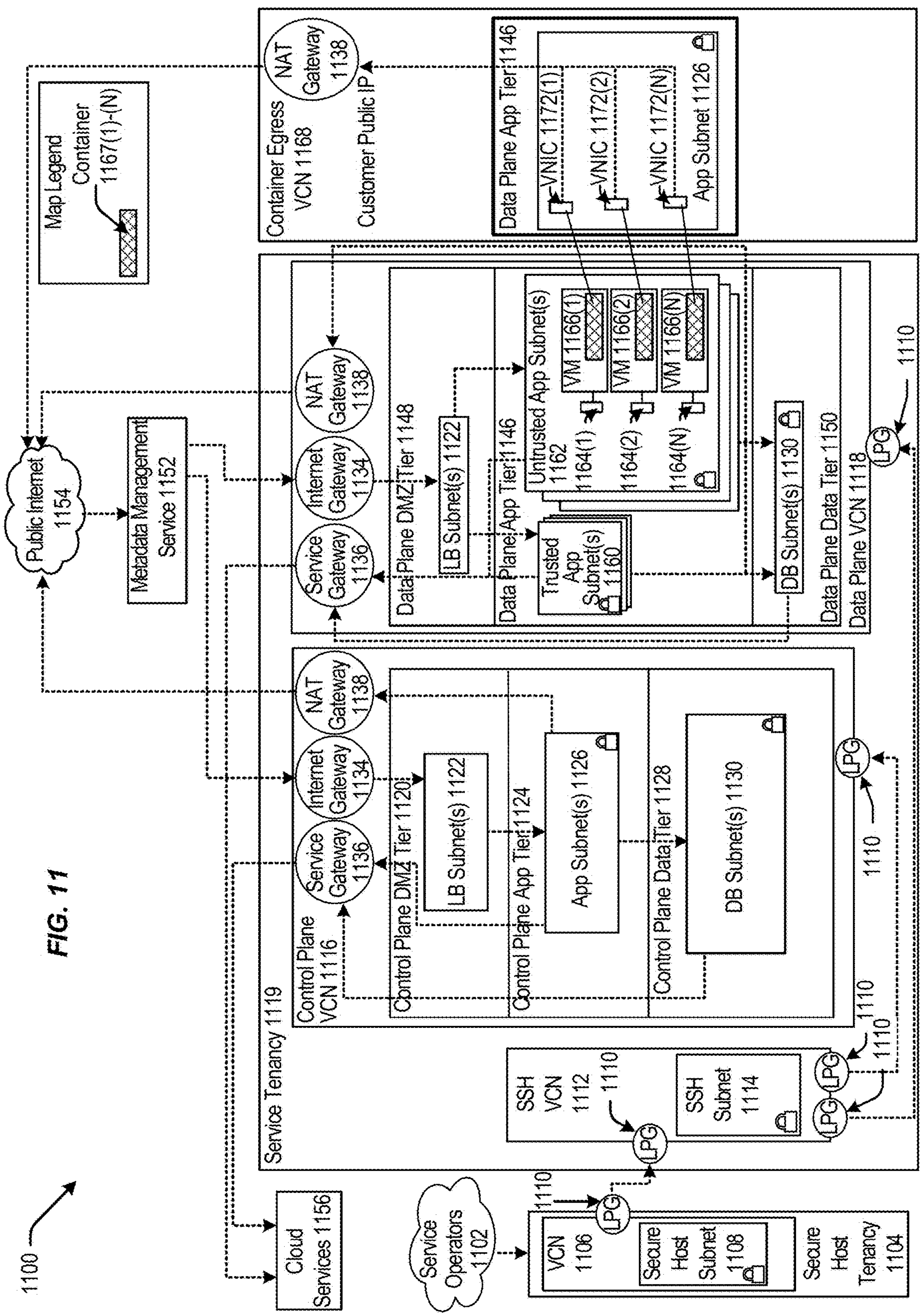
FIG. 11 is a block diagram illustrating another pattern for implementing a cloud infrastructure as a service system, according to at least one embodiment.

FIG. 11 is a block diagram 1100 illustrating another example pattern of an IaaS architecture, according to at least one embodiment. Service operators 1102 (e.g., service operators 802 of FIG. 8) can be communicatively coupled to a secure host tenancy 1104 (e.g., the secure host tenancy 804 of FIG. 8) that can include a virtual cloud network (VCN) 1106 (e.g., the VCN 806 of FIG. 8) and a secure host subnet 1108 (e.g., the secure host subnet 808 of FIG. 8). The VCN 1106 can include an LPG 1110 (e.g., the LPG 810 of FIG. 8) that can be communicatively coupled to an SSH VCN 1112 (e.g., the SSH VCN 812 of FIG. 8) via an LPG 1110 contained in the SSH VCN 1112. The SSH VCN 1112 can include an SSH subnet 1114 (e.g., the SSH subnet 814 of FIG. 8), and the SSH VCN 1112 can be communicatively coupled to a control plane VCN 1116 (e.g., the control plane VCN 816 of FIG. 8) via an LPG 1110 contained in the control plane VCN 1116 and to a data plane VCN 1118 (e.g., the data plane 818 of FIG. 8) via an LPG 1110 contained in the data plane VCN 1118. The control plane VCN 1116 and the data plane VCN 1118 can be contained in a service tenancy 1119 (e.g., the service tenancy 819 of FIG. 8).

The control plane VCN 1116 can include a control plane DMZ tier 1120 (e.g., the control plane DMZ tier 820 of FIG. 8) that can include LB subnet(s) 1122 (e.g., LB subnet(s) 822 of FIG. 8), a control plane app tier 1124 (e.g., the control plane app tier 824 of FIG. 8) that can include app subnet(s) 1126 (e.g., app subnet(s) 826 of FIG. 8), a control plane data tier 1128 (e.g., the control plane data tier 828 of FIG. 8) that can include DB subnet(s) 1130 (e.g., DB subnet(s) 1030 of FIG. 10). The LB subnet(s) 1122 contained in the control plane DMZ tier 1120 can be communicatively coupled to the app subnet(s) 1126 contained in the control plane app tier 1124 and to an Internet gateway 1134 (e.g., the Internet gateway 834 of FIG. 8) that can be contained in the control plane VCN 1116, and the app subnet(s) 1126 can be communicatively coupled to the DB subnet(s) 1130 contained in the control plane data tier 1128 and to a service gateway 1136 (e.g., the service gateway of FIG. 8) and a network address translation (NAT) gateway 1138 (e.g., the NAT gateway 838 of FIG. 8). The control plane VCN 1116 can include the service gateway 1136 and the NAT gateway 1138.

The data plane VCN 1118 can include a data plane app tier 1146 (e.g., the data plane app tier 846 of FIG. 8), a data plane DMZ tier 1148 (e.g., the data plane DMZ tier 848 of FIG. 8), and a data plane data tier 1150 (e.g., the data plane data tier 850 of FIG. 8). The data plane DMZ tier 1148 can include LB subnet(s) 1122 that can be communicatively coupled to trusted app subnet(s) 1160 (e.g., trusted app subnet(s) 1060 of FIG. 10) and untrusted app subnet(s) 1162 (e.g., untrusted app subnet(s) 1062 of FIG. 10) of the data plane app tier 1146 and the Internet gateway 1134 contained in the data plane VCN 1118. The trusted app subnet(s) 1160 can be communicatively coupled to the service gateway 1136 contained in the data plane VCN 1118, the NAT gateway 1138 contained in the data plane VCN 1118, and DB subnet(s) 1130 contained in the data plane data tier 1150. The untrusted app subnet(s) 1162 can be communicatively coupled to the service gateway 1136 contained in the data plane VCN 1118 and DB subnet(s) 1130 contained in the data plane data tier 1150. The data plane data tier 1150 can include DB subnet(s) 1130 that can be communicatively coupled to the service gateway 1136 contained in the data plane VCN 1118.

The untrusted app subnet(s) 1162 can include primary VNICs 1164(1)-(N) that can be communicatively coupled to tenant virtual machines (VMs) 1166(1)-(N) residing within the untrusted app subnet(s) 1162. Each tenant VM 1166(1)-(N) can run code in a respective container 1167(1)-(N), and be communicatively coupled to an app subnet 1126 that can be contained in a data plane app tier 1146 that can be contained in a container egress VCN 1168. Respective secondary VNICs 1172(1)-(N) can facilitate communication between the untrusted app subnet(s) 1162 contained in the data plane VCN 1118 and the app subnet contained in the container egress VCN 1168. The container egress VCN can include a NAT gateway 1138 that can be communicatively coupled to public Internet 1154 (e.g., public Internet 854 of FIG. 8).

The Internet gateway 1134 contained in the control plane VCN 1116 and contained in the data plane VCN 1118 can be communicatively coupled to a metadata management service 1152 (e.g., the metadata management system 852 of FIG. 8) that can be communicatively coupled to public Internet 1154. Public Internet 1154 can be communicatively coupled to the NAT gateway 1138 contained in the control plane VCN 1116 and contained in the data plane VCN 1118. The service gateway 1136 contained in the control plane VCN 1116 and contained in the data plane VCN 1118 can be communicatively coupled to cloud services 1156.

In some examples, the pattern illustrated by the architecture of block diagram 1100 of FIG. 11 may be considered an exception to the pattern illustrated by the architecture of block diagram 1000 of FIG. 10 and may be desirable for a customer of the IaaS provider if the IaaS provider cannot directly communicate with the customer (e.g., a disconnected region). The respective containers 1167(1)-(N) that are contained in the VMs 1166(1)-(N) for each customer can be accessed in real-time by the customer. The containers 1167(1)-(N) may be configured to make calls to respective secondary VNICs 1172(1)-(N) contained in app subnet(s) 1126 of the data plane app tier 1146 that can be contained in the container egress VCN 1168. The secondary VNICs 1172(1)-(N) can transmit the calls to the NAT gateway 1138 that may transmit the calls to public Internet 1154. In this example, the containers 1167(1)-(N) that can be accessed in real-time by the customer can be isolated from the control plane VCN 1116 and can be isolated from other entities contained in the data plane VCN 1118. The containers 1167(1)-(N) may also be isolated from resources from other customers.

In other examples, the customer can use the containers 1167(1)-(N) to call cloud services 1156. In this example, the customer may run code in the containers 1167(1)-(N) that requests a service from cloud services 1156. The containers 1167(1)-(N) can transmit this request to the secondary VNICs 1172(1)-(N) that can transmit the request to the NAT gateway that can transmit the request to public Internet 1154. Public Internet 1154 can transmit the request to LB subnet(s) 1122 contained in the control plane VCN 1116 via the Internet gateway 1134. In response to determining the request is valid, the LB subnet(s) can transmit the request to app subnet(s) 1126 that can transmit the request to cloud services 1156 via the service gateway 1136.

It should be appreciated that IaaS architectures 800, 900, 1000, 1100 depicted in the figures may have other components than those depicted. Further, the embodiments shown in the figures are only some examples of a cloud infrastructure system that may incorporate an embodiment of the disclosure. In some other embodiments, the IaaS systems may have more or fewer components than shown in the figures, may combine two or more components, or may have a different configuration or arrangement of components.

In certain embodiments, the IaaS systems described herein may include a suite of applications, middleware, and database service offerings that are delivered to a customer in a self-service, subscription-based, elastically scalable, reliable, highly available, and secure manner. An example of such an IaaS system is the Oracle Cloud Infrastructure (OCI) provided by the present assignee.

Figure 12:
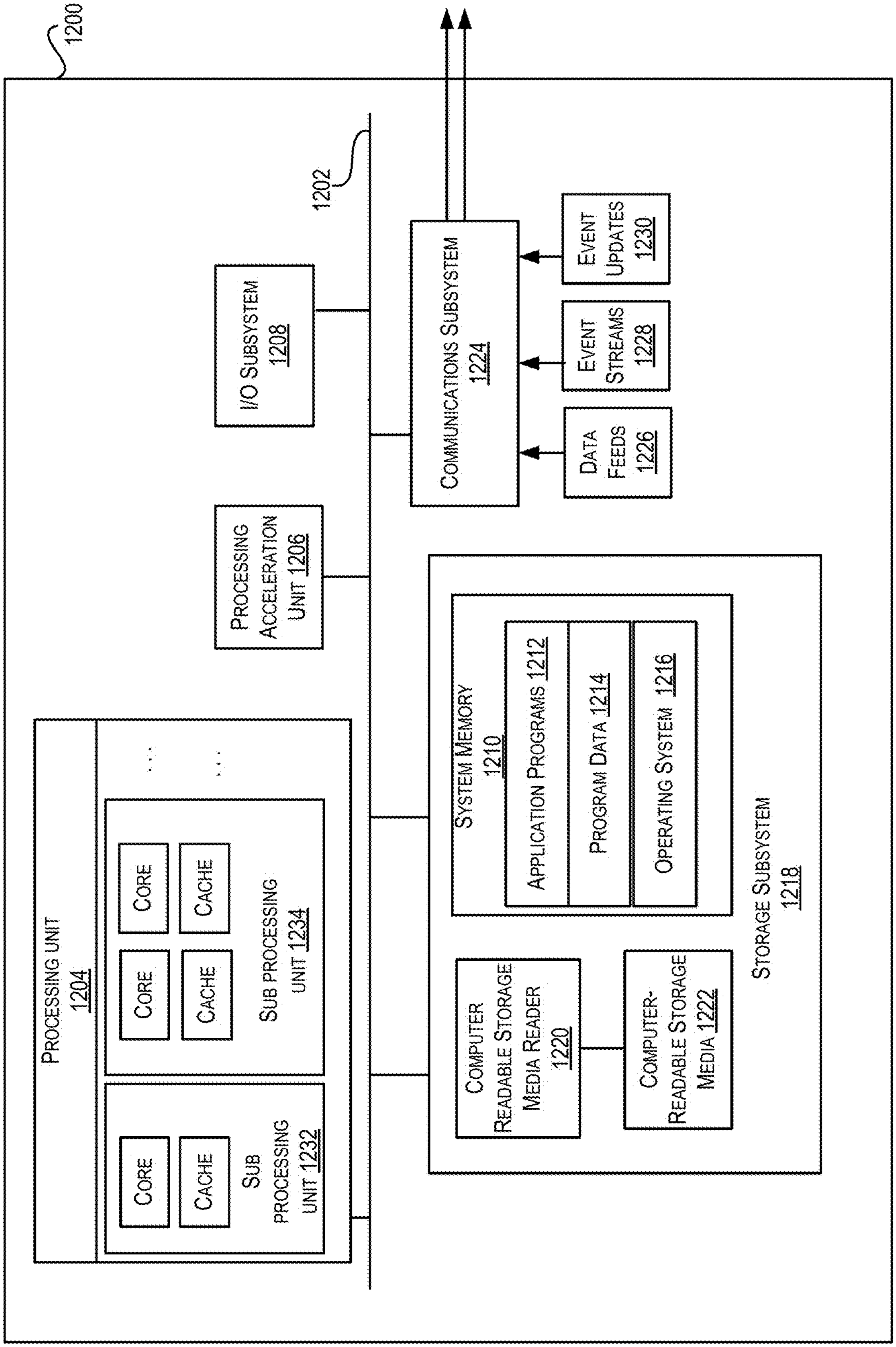
FIG. 12 is a block diagram illustrating an example computer system, according to at least one embodiment.

FIG. 12 illustrates an example computer system 1200, in which various embodiments may be implemented. The system 1200 may be used to implement any of the computer systems described above. As shown in the figure, computer system 1200 includes a processing unit 1204 that communicates with a number of peripheral subsystems via a bus subsystem 1202. These peripheral subsystems may include a processing acceleration unit 1206, an I/O subsystem 1208, a storage subsystem 1218 and a communications subsystem 1224. Storage subsystem 1218 includes tangible computer-readable storage media 1222 and a system memory 1210.

Bus subsystem 1202 provides a mechanism for letting the various components and subsystems of computer system 1200 communicate with each other as intended. Although bus subsystem 1202 is shown schematically as a single bus, alternative embodiments of the bus subsystem may utilize multiple buses. Bus subsystem 1202 may be any of several types of bus structures including a memory bus or memory controller, a peripheral bus, and a local bus using any of a variety of bus architectures. For example, such architectures may include an Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, which can be implemented as a Mezzanine bus manufactured to the IEEE P1386.1 standard.

Processing unit 1204, which can be implemented as one or more integrated circuits (e.g., a conventional microprocessor or microcontroller), controls the operation of computer system 1200. One or more processors may be included in processing unit 1204. These processors may include single core or multicore processors. In certain embodiments, processing unit 1204 may be implemented as one or more independent processing units 1232 and/or 1234 with single or multicore processors included in each processing unit. In other embodiments, processing unit 1204 may also be implemented as a quad-core processing unit formed by integrating two dual-core processors into a single chip.

In various embodiments, processing unit 1204 can execute a variety of programs in response to program code and can maintain multiple concurrently executing programs or processes. At any given time, some or all of the program code to be executed can be resident in processor(s) 1204 and/or in storage subsystem 1218. Through suitable programming, processor(s) 1204 can provide various functionalities described above. Computer system 1200 may additionally include a processing acceleration unit 1206, which can include a digital signal processor (DSP), a special-purpose processor, and/or the like.

I/O subsystem 1208 may include user interface input devices and user interface output devices. User interface input devices may include a keyboard, pointing devices such as a mouse or trackball, a touchpad or touch screen incorporated into a display, a scroll wheel, a click wheel, a dial, a button, a switch, a keypad, audio input devices with voice command recognition systems, microphones, and other types of input devices. User interface input devices may include, for example, motion sensing and/or gesture recognition devices such as the Microsoft Kinect® motion sensor that enables users to control and interact with an input device, such as the Microsoft Xbox®360 game controller, through a natural user interface using gestures and spoken commands. User interface input devices may also include eye gesture recognition devices such as the Google Glass® blink detector that detects eye activity (e.g., 'blinking' while taking pictures and/or making a menu selection) from users and transforms the eye gestures as input into an input device (e.g., Google Glass®). Additionally, user interface input devices may include voice recognition sensing devices that enable users to interact with voice recognition systems (e.g., Siri® navigator), through voice commands.

User interface input devices may also include, without limitation, three dimensional (3D) mice, joysticks or pointing sticks, gamepads and graphic tablets, and audio/visual devices such as speakers, digital cameras, digital camcorders, portable media players, webcams, image scanners, fingerprint scanners, barcode reader 3D scanners, 3D printers, laser rangefinders, and eye gaze tracking devices. Additionally, user interface input devices may include, for example, medical imaging input devices such as computed tomography, magnetic resonance imaging, position emission tomography, medical ultrasonography devices. User interface input devices may also include, for example, audio input devices such as MIDI keyboards, digital musical instruments and the like.

User interface output devices may include a display subsystem, indicator lights, or non-visual displays such as audio output devices, etc. The display subsystem may be a cathode ray tube (CRT), a flat-panel device, such as that using a liquid crystal display (LCD) or plasma display, a projection device, a touch screen, and the like. In general, use of the term "output device" is intended to include all possible types of devices and mechanisms for outputting information from computer system 1200 to a user or other computer. For example, user interface output devices may include, without limitation, a variety of display devices that visually convey text, graphics and audio/video information such as monitors, printers, speakers, headphones, automotive navigation systems, plotters, voice output devices, and modems.

Computer system 1200 may comprise a storage subsystem 1218 that provides a tangible non-transitory computer-readable storage medium for storing software and data constructs that provide the functionality of the embodiments described in this disclosure. The software can include programs, code modules, instructions, scripts, etc., that when executed by one or more cores or processors of processing unit 1204 provide the functionality described above. Storage subsystem 1218 may also provide a repository for storing data used in accordance with the present disclosure.

As depicted in the example in FIG. 12, storage subsystem 1218 can include various components including a system memory 1210, computer-readable storage media 1222, and a computer readable storage media reader 1220. System memory 1210 may store program instructions that are loadable and executable by processing unit 1204. System memory 1210 may also store data that is used during the execution of the instructions and/or data that is generated during the execution of the program instructions. Various different kinds of programs may be loaded into system memory 1210 including but not limited to client applications, Web browsers, mid-tier applications, relational database management systems (RDBMS), virtual machines, containers, etc.

System memory 1210 may also store an operating system 1216. Examples of operating system 1216 may include various versions of Microsoft Windows®, Apple Macintosh®, and/or Linux operating systems, a variety of commercially-available UNIX® or UNIX-like operating systems (including without limitation the variety of GNU/Linux operating systems, the Google Chrome® OS, and the like) and/or mobile operating systems such as iOS, Windows® Phone, Android® OS, BlackBerry® OS, and Palm® OS operating systems. In certain implementations where computer system 1200 executes one or more virtual machines, the virtual machines along with their guest operating systems (GOSs) may be loaded into system memory 1210 and executed by one or more processors or cores of processing unit 1204.

System memory 1210 can come in different configurations depending upon the type of computer system 1200. For example, system memory 1210 may be volatile memory (such as random access memory (RAM)) and/or non-volatile memory (such as read-only memory (ROM), flash memory, etc.) Different types of RAM configurations may be provided including a static random access memory (SRAM), a dynamic random access memory (DRAM), and others. In some implementations, system memory 1210 may include a basic input/output system (BIOS) containing basic routines that help to transfer information between elements within computer system 1200, such as during start-up.

Computer-readable storage media 1222 may represent remote, local, fixed, and/or removable storage devices plus storage media for temporarily and/or more permanently containing, storing, computer-readable information for use by computer system 1200 including instructions executable by processing unit 1204 of computer system 1200.

Computer-readable storage media 1222 can include any appropriate media known or used in the art, including storage media and communication media, such as but not limited to, volatile and non-volatile, removable and non-removable media implemented in any method or technology for storage and/or transmission of information. This can include tangible computer-readable storage media such as RAM, ROM, electronically erasable programmable ROM (EEPROM), flash memory or other memory technology, CD-ROM, digital versatile disk (DVD), or other optical storage, magnetic cassettes, magnetic tape, magnetic disk storage or other magnetic storage devices, or other tangible computer readable media.

By way of example, computer-readable storage media 1222 may include a hard disk drive that reads from or writes to non-removable, nonvolatile magnetic media, a magnetic disk drive that reads from or writes to a removable, non-volatile magnetic disk, and an optical disk drive that reads from or writes to a removable, nonvolatile optical disk such as a CD ROM, DVD, and Blu-Ray® disk, or other optical media. Computer-readable storage media 1222 may include, but is not limited to, Zip® drives, flash memory cards, universal serial bus (USB) flash drives, secure digital (SD) cards, DVD disks, digital video tape, and the like. Computer-readable storage media 1222 may also include, solid-state drives (SSD) based on non-volatile memory such as flash-memory based SSDs, enterprise flash drives, solid state ROM, and the like, SSDs based on volatile memory such as solid state RAM, dynamic RAM, static RAM, DRAM-based SSDs, magnetoresistive RAM (MRAM) SSDs, and hybrid SSDs that use a combination of DRAM and flash memory based SSDs. The disk drives and their associated computer-readable media may provide non-volatile storage of computer-readable instructions, data structures, program modules, and other data for computer system 1200.

Machine-readable instructions executable by one or more processors or cores of processing unit 1204 may be stored on a non-transitory computer-readable storage medium. A non-transitory computer-readable storage medium can include physically tangible memory or storage devices that include volatile memory storage devices and/or non-volatile storage devices. Examples of non-transitory computer-readable storage medium include magnetic storage media (e.g., disk or tapes), optical storage media (e.g., DVDs, CDs), various types of RAM, ROM, or flash memory, hard drives, floppy drives, detachable memory drives (e.g., USB drives), or other type of storage device.

Communications subsystem 1224 provides an interface to other computer systems and networks. Communications subsystem 1224 serves as an interface for receiving data from and transmitting data to other systems from computer system 1200. For example, communications subsystem 1224 may enable computer system 1200 to connect to one or more devices via the Internet. In some embodiments communications subsystem 1224 can include radio frequency (RF) transceiver components for accessing wireless voice and/or data networks (e.g., using cellular telephone technology, advanced data network technology, such as 3G, 4G or EDGE (enhanced data rates for global evolution), WiFi (IEEE 802.11 family standards, or other mobile communication technologies, or any combination thereof)), global positioning system (GPS) receiver components, and/or other components. In some embodiments communications subsystem 1224 can provide wired network connectivity (e.g., Ethernet) in addition to or instead of a wireless interface.

In some embodiments, communications subsystem 1224 may also receive input communication in the form of structured and/or unstructured data feeds 1226, event streams 1228, event updates 1230, and the like on behalf of one or more users who may use computer system 1200.

By way of example, communications subsystem 1224 may be configured to receive data feeds 1226 in real-time from users of social networks and/or other communication services such as Twitter® feeds, Facebook® updates, web feeds such as Rich Site Summary (RSS) feeds, and/or real-time updates from one or more third party information sources.

Additionally, communications subsystem 1224 may also be configured to receive data in the form of continuous data streams, which may include event streams 1228 of real-time events and/or event updates 1230, that may be continuous or unbounded in nature with no explicit end. Examples of applications that generate continuous data may include, for example, sensor data applications, financial tickers, network performance measuring tools (e.g., network monitoring and traffic management applications), clickstream analysis tools, automobile traffic monitoring, and the like.

Communications subsystem 1224 may also be configured to output the structured and/or unstructured data feeds 1226, event streams 1228, event updates 1230, and the like to one or more databases that may be in communication with one or more streaming data source computers coupled to computer system 1200.

Computer system 1200 can be one of various types, including a handheld portable device (e.g., an iPhone® cellular phone, an iPad® computing tablet, a PDA), a wearable device (e.g., a Google Glass® head mounted display), a PC, a workstation, a mainframe, a kiosk, a server rack, or any other data processing system.

Due to the ever-changing nature of computers and networks, the description of computer system 1200 depicted in the figure is intended only as a specific example. Many other configurations having more or fewer components than the system depicted in the figure are possible. For example, customized hardware might also be used and/or particular elements might be implemented in hardware, firmware, software (including applets), or a combination. Further, connection to other computing devices, such as network input/output devices, may be employed. Based on the disclosure and teachings provided herein, a person of ordinary skill in the art will appreciate other ways and/or methods to implement the various embodiments.

Although specific embodiments have been described, various modifications, alterations, alternative constructions, and equivalents are also encompassed within the scope of the disclosure. Embodiments are not restricted to operation within certain specific data processing environments, but are free to operate within a plurality of data processing environments. Additionally, although embodiments have been described using a particular series of transactions and steps, it should be apparent to those skilled in the art that the scope of the present disclosure is not limited to the described series of transactions and steps. Various features and aspects of the above-described embodiments may be used individually or jointly.

Further, while embodiments have been described using a particular combination of hardware and software, it should be recognized that other combinations of hardware and software are also within the scope of the present disclosure. Embodiments may be implemented only in hardware, or only in software, or using combinations thereof. The various processes described herein can be implemented on the same processor or different processors in any combination. Accordingly, where components or services are described as being configured to perform certain operations, such configuration can be accomplished, e.g., by designing electronic circuits to perform the operation, by programming programmable electronic circuits (such as microprocessors) to perform the operation, or any combination thereof. Processes can communicate using a variety of techniques including but not limited to conventional techniques for inter process communication, and different pairs of processes may use different techniques, or the same pair of processes may use different techniques at different times.

The specification and drawings are, accordingly, to be regarded in an illustrative rather than a restrictive sense. It will, however, be evident that additions, subtractions, deletions, and other modifications and changes may be made thereunto without departing from the broader spirit and scope as set forth in the claims. Thus, although specific disclosure embodiments have been described, these are not intended to be limiting. Various modifications and equivalents are within the scope of the following claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is intended to be understood within the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Preferred embodiments of this disclosure are described herein, including the best mode known for carrying out the disclosure. Variations of those preferred embodiments may become apparent to those of ordinary skill in the art upon reading the foregoing description. Those of ordinary skill should be able to employ such variations as appropriate and the disclosure may be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein.

All references, including publications, patent applications, and patents, cited herein are hereby incorporated by reference to the same extent as if each reference were individually and specifically indicated to be incorporated by reference and were set forth in its entirety herein.

In the foregoing specification, aspects of the disclosure are described with reference to specific embodiments thereof, but those skilled in the art will recognize that the disclosure is not limited thereto. Various features and aspects of the above-described disclosure may be used individually or jointly. Further, embodiments can be utilized in any number of environments and applications beyond those described herein without departing from the broader spirit and scope of the specification. The specification and drawings are, accordingly, to be regarded as illustrative rather than restrictive.

Although specific embodiments have been described, various modifications, alterations, alternative constructions, and equivalents are also encompassed within the scope of the disclosure. Embodiments are not restricted to operation within certain specific data processing environments but are free to operate within a plurality of data processing environments. Additionally, although embodiments have been described using a particular series of transactions and steps, it should be apparent to those skilled in the art that the scope of the present disclosure is not limited to the described series of transactions and steps. Various features and aspects of the above-described embodiments may be used individually or jointly.

Further, while embodiments have been described using a particular combination of hardware and software, it should be recognized that other combinations of hardware and software are also within the scope of the present disclosure. Embodiments may be implemented only in hardware, or only in software, or using combinations thereof. The various processes described herein can be implemented on the same processor or different processors in any combination. Accordingly, where components or services are described as being configured to perform certain operations, such configuration can be accomplished, e.g., by designing electronic circuits to perform the operation, by programming programmable electronic circuits (such as microprocessors) to perform the operation, or any combination thereof. Processes can communicate using a variety of techniques including but not limited to conventional techniques for inter process communication, and different pairs of processes may use different techniques, or the same pair of processes may use different techniques at different times.

The specification and drawings are, accordingly, to be regarded in an illustrative rather than a restrictive sense. It will, however, be evident that additions, subtractions, deletions, and other modifications and changes may be made thereunto without departing from the broader spirit and scope as set forth in the claims. Thus, although specific disclosure embodiments have been described, these are not intended to be limiting. Various modifications and equivalents are within the scope of the following claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments and does not pose a limitation on the scope of the disclosure unless otherwise claimed. No language in the specification should be construed as indicating any non-claimed element as essential to the practice of the disclosure.

As used herein, when an action is "based on" something, this means the action is based at least in part on at least a part of the something. As used herein, the terms "substantially," "approximately" and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 5, and 10 percent.

Disjunctive language such as the phrase "at least one of X, Y, or Z," unless specifically stated otherwise, is intended to be understood within the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Preferred embodiments of this disclosure are described herein, including the best mode known for carrying out the disclosure. Variations of those preferred embodiments may become apparent to those of ordinary skill in the art upon reading the foregoing description. Those of ordinary skill should be able to employ such variations as appropriate and the disclosure may be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein.

All references, including publications, patent applications, and patents, cited herein are hereby incorporated by reference to the same extent as if each reference were individually and specifically indicated to be incorporated by reference and were set forth in its entirety herein.

In the foregoing specification, aspects of the disclosure are described with reference to specific embodiments thereof, but those skilled in the art will recognize that the disclosure is not limited thereto. Various features and aspects of the above-described disclosure may be used individually or jointly. Further, embodiments can be utilized in any number of environments and applications beyond those described herein without departing from the broader spirit and scope of the specification. The specification and drawings are, accordingly, to be regarded as illustrative rather than restrictive.

What is claimed is:

1. A computer-implemented method for controlling a client device, the method comprising:

providing, from the client device to a computing system, a first notification that notifies the computing system that an audio data stream comprising a plurality of data messages has been initiated by the client device;

providing, from the client device to the computing system, a first data message comprising a first sequence number, a first timestamp, and a first payload, the first sequence number indicating a first position within the audio data stream to which the first payload corresponds;

storing, as a first buffered data message, the first data message in a buffer of the client device, the buffer comprising one or more buffered data messages;

determining that a first error condition for the first data message has occurred based on at least one of the one or more buffered data messages or a first acknowledgement status of the first data message; and responsive to determining that the first error condition for the first data message has occurred, re-providing, from the client device to the computing system, the first data message.

2. The computer-implemented method of claim 1, wherein the audio data stream is associated with an in-progress audio recording being recorded by the client device, and wherein:

the first payload comprises a portion of the in-progress audio recording, wherein the in-progress audio recording comprises audio corresponding to a conversation involving a patient;

and further comprising:

receiving, by the client device and from the computing system, a clinical note based on the conversation, the clinical note based on a transcript generated using the in-progress audio recording.

3. The computer-implemented method of claim 1, wherein providing the first notification to the computing system causes the computing system to initiate a process for generating an audio data file.

4. The computer-implemented method of claim 1, wherein:

determining the first error condition for the first data message comprises determining an age for the first buffered data message based on the first timestamp, wherein the age for the first buffered data message is based on a difference between a current time timestamp and the first timestamp; and determining that the age for the first buffered data message exceeds a predetermined threshold.

5. The computer-implemented method of claim 1, wherein:

each buffered data message of the one or more buffered data messages has a respective timestamp; and determining the first error condition for the first data message comprises:

determining the oldest buffered data message in the buffer based on the respective timestamps of the one or more buffered data messages, the oldest buffered data message comprising a timestamp of the oldest buffered data message; and determining that the oldest buffered data message has an age exceeding a predetermined threshold, wherein the age for the oldest buffered data message is based on a difference between a current time timestamp and the timestamp of the oldest buffered data message.

6. The computer-implemented method of claim 1, wherein determining the first error condition for the first data message comprises determining that, after a predetermined period of time, the first acknowledgement status does not include receipt of an acknowledgement of the first data message.

7. The computer-implemented method of claim 1, wherein determining the first error condition for the first data message comprises:

receiving a first indication that a network connection with the computing system is unavailable;

receiving a second indication that the network connection with the computing system has become available following a period of unavailability; and determining, following the period of unavailability, that the first acknowledgement status does not include receipt of an acknowledgement of the first data message.

8. The computer-implemented method of claim 1, further comprising:

after re-providing the first data message, providing, from the client device to the computing system, a second notification that notifies the computing system that the audio data stream has been terminated by the client device.

9. A client device comprising:

one or more non-transitory computer-readable media; and one or more processors communicatively coupled to the one or more non-transitory computer-readable media, the one or more processors configured to execute processor-executable instructions stored in the non-transitory computer-readable media to:

provide, from the client device to a computing system, a first notification that notifies the computing system that an audio data stream comprising a plurality of data messages has been initiated by the client device;

provide, from the client device to the computing system, a first data message comprising a first sequence number, a first timestamp, and a first payload, the first sequence number indicating a first position within the audio data stream to which the first payload corresponds;

store, as a first buffered data message, the first data message in a buffer of the client device, the buffer comprising one or more buffered data messages;

determine that a first error condition for the first data message has occurred based on at least one of the one or more buffered data messages or a first acknowledgement status of the first data message; and responsive to determining that the first error condition for the first data message has occurred, re-provide, from the client device to the computing system, the first data message.

10. The client device of claim 9, further comprising additional processor-executable instructions stored in the non-transitory computer-readable media to:

receive, from the computing system, an acknowledgment of the first data message; and responsive to receiving the acknowledgement, remove the first data message from the buffer.

11. The client device of claim 9, further comprising additional processor-executable instructions stored in the non-transitory computer-readable media to:

provide, from the client device to the computing system, a second data message comprising a second sequence number, a second timestamp, and a second payload, the second sequence number indicating a second position within the audio data stream to which the second payload corresponds, the second position being a position after the first position;

store, as a second buffered data message, the second data message in the buffer;

provide, from the client device to the computing system, a third data message comprising a third sequence number, a third timestamp, and a third payload, the third sequence number indicating a third position within the audio data stream to which the third payload corresponds, the third position being a position after the first position;

store, as a third buffered data message, the third data message in the buffer;

receive, from the computing system, an acknowledgment of the second data message; and remove the second data message from the buffer.

12. The client device of claim 9, wherein:

the first data message further comprises a session identifier, the session identifier associated with a first session managed by the computing system;

the audio data stream is associated with the first session; and the first session is associated with a plurality of client devices including the client device.

13. The client device of claim 9, further comprising additional processor-executable instructions stored in the non-transitory computer-readable media to:

provide, from the client device to the computing system, a second data message comprising a second sequence number, a second timestamp, and a second payload, the second sequence number indicating a second position within the audio data stream to which the second payload corresponds, the second position being a position after the first position;

store, as a second buffered data message, the second data message in the buffer;

provide, from the client device to the computing system, a third data message comprising a third sequence number, a third timestamp, and a third payload, the third sequence number indicating a third position within the audio data stream to which the third payload corresponds, the third position being a position after the second position;

store, as a third buffered data message, the third data message in the buffer;

receive, from the computing system, an acknowledgment of the third data message; and remove the third data message from the buffer.

14. The client device of claim 9, further comprising additional processor-executable instructions stored in the non-transitory computer-readable media to:

provide, from the client device to the computing system, a second data message comprising a second sequence number, a second timestamp, and a second payload, the second sequence number indicating a second position within the audio data stream to which the second payload corresponds, the second position being a position after the first position;

store, as a second buffered data message, the second data message in the buffer;

provide, to the computing system, a second notification that notifies the computing system that the audio data stream has been terminated by the client device;

determine that an age of the second buffered data message based on the second timestamp exceeds a predetermined threshold, wherein the age of the second buffered data message is based on a difference between a current time timestamp and the second timestamp; and in response to the age exceeding the predetermined threshold, re-provide, from the client device to the computing system, the second data message.

15. The client device of claim 9, further comprising additional processor-executable instructions stored in the non-transitory computer-readable media to:

provide, from the client device to the computing system, a second notification to pause the audio data stream including a second sequence number that is greater than the first sequence number; and provide, from the client device to the computing system, a second data message comprising a third sequence number that is greater than the second sequence number, a second timestamp, and a second payload, the third sequence number indicating a second position within the audio data stream to which the second payload corresponds, the second position being a position after the first position.

16. The client device of claim 9, further comprising additional processor-executable instructions stored in the non-transitory computer-readable media to:

provide, from the client device to the computing system, a second notification to cancel the audio data stream; and remove, from the buffer, all buffered data messages.

17. The client device of claim 9, wherein:

the computing system assembles an audio file based on the audio data stream, wherein the assembled audio file is generated by:

receiving, from the client device, the first notification that the audio data stream has been initiated by the client device;

receiving, from the client device, the first data message;

storing first information about the first data message including the first sequence number and the first timestamp;

storing the first data message using a storage system;

providing, to the client device, a first acknowledgement;

receiving, from the client device, a second data message comprising a second sequence number, a second timestamp, and a second payload, the second sequence number indicating a second position within the audio data stream to which the second payload corresponds, the second position being a position after the first position;

storing second information about the second data message including the second sequence number and the second timestamp;

storing the second data message using the storage system;

providing, to the client device, a second acknowledgement of the second data message;

receiving, from the client device, a second notification that the audio data stream has been terminated by the client device; and assembling the audio file using at least the first data message and the second data message stored in the storage system using an ordering determined use the respective sequence numbers of the first data message and the second data message.

18. One or more non-transitory computer-readable storage media storing processor-executable instructions that, when executed by one or more processors, cause the one or more processors to perform operations comprising:

receiving, from a client device, a first notification that an audio data stream comprising a plurality of data messages has been initiated by the client device;

receiving, from the client device, a first data message comprising a first sequence number, a first timestamp, and a first payload, the first sequence number indicating a first position within the audio data stream to which the first payload corresponds;

storing first information about the first data message including the first sequence number and the first timestamp;

storing the first data message using a storage system;

providing, to the client device, a first acknowledgement of the first data message;

receiving, from the client device, a second data message comprising a second sequence number, a second timestamp, and a second payload, the second sequence number indicating a second position within the audio data stream to which the second payload corresponds, the second position being a position after the first position;

storing second information about the second data message including the second sequence number and the second timestamp;

storing the second data message using the storage system;

providing, to the client device, a second acknowledgement of the second data message;

receiving, from the client device, a second notification that the audio data stream has been terminated by the client device; and assembling an audio stream using the first data message and the second data message stored in the storage system using an ordering determined use the respective sequence numbers of the first data message and the second data message.

19. The one or more non-transitory computer-readable storage media of claim 18, wherein:

the first data message and the second data message each include a portion of a streaming audio recording including one or more words spoken by a healthcare provider during a clinical encounter; and further comprising:

outputting the audio stream to an ambient audio summary generation service including a transcription service and a clinical note generation service, wherein the clinical note generation service is configured to generate a clinical note based on the clinical encounter using a transcript generated by the transcription service.

20. The one or more non-transitory computer-readable storage media of claim 18, comprising additional instructions configured to cause the one or more processors to:

re-receive, from the client device, the first data message;

determine that the first data message has already been received; and securely delete the re-received first data message.

* * * * *